United States Patent [19]
Abdel-Rahman et al.

[11] Patent Number: 5,389,621
[45] Date of Patent: Feb. 14, 1995

[54] METHOD OF ENHANCING THE ANTICOAGULANT EFFECTS OF ASPIRIN USING SALICYLAMIDE

[75] Inventors: Mohamed S. Abdel-Rahman, Montville, N.J.; Maged M. Rizk, Croton-On-Hudson, N.Y.

[73] Assignee: University of Medicine and Dentistry of New Jersey, Newark, N.J.

[21] Appl. No.: 199,345

[22] Filed: Feb. 18, 1994

Related U.S. Application Data

[63] Continuation of Ser. No. 977,897, Nov. 18, 1992, abandoned.

[51] Int. Cl.$^6$ .................. A61K 31/60; A61K 31/615; A61K 31/16
[52] U.S. Cl. .................. 514/159; 514/162; 514/629; 514/630
[58] Field of Search ................ 514/159, 162, 629, 630

[56] References Cited

U.S. PATENT DOCUMENTS

| | | | |
|---|---|---|---|
| 4,329,986 | 5/1982 | Babb | 128/214 |
| 4,528,178 | 7/1985 | Babb | 424/7.1 |
| 4,885,287 | 12/1989 | Hussain et al. | 514/159 |
| 4,943,565 | 7/1990 | Tencza et al. | 514/629 |

OTHER PUBLICATIONS

Abdel-Rahman, M. et al., Can. J. Physiol. Pharmacol. 69, pp. 1436–1442, 1992.
Ali, M. et al., Prostaglandin Med. 3, pp. 327–332, 1979.
Al-Nibdgurtm G., et al., Proc. Soc. Exp. Biol. Med., 1B3, pp. 632–636, 1970.
Austen, K., Drugs 33 (supp.) pp. 10–17, 1987.
Bakar, S. K., et al., J. Pharm. Sci., 72, pp. 1020–1023, 1983.
Barr, W. et al., Pharmacokinetics, A Modern View, pp. 426–429, Plenum press, New York, 1969.
Barr, W., Drug Inf. Bull. pp. 27–45 (Jan./Jun. 1969).
Barr, W. et al., Rev. Can. Biol., 32, (suppl.) pp. 31–42 1973.
Batterman, R. et al., J. Am. Med. Assoc., 159, pp. 1619–1622, 1955.
Baven, E. et al., J. Pharm. Pharmacol., 6 pp. 872–878, 1952.
Berger, F., Proc. Soc. Exp. Biol. Med., 87, pp. 449–451, 1954.
Borovsky, M., Am. J. Dis. Child., 100, pp. 23–30 1960.
Bradon, R. et al., Ther; Drug Monit., 7, pp. 216–221, 1985.
Braden, G., et al., Circulation, 84, pp. 679–685 (supp.) 1991.
Brandon, R., et al., Ther. Drug Monit. 7, pp. 216–221 (1985).
Brecher G. et al., Am. U. Clin Path. 23, pp. 15–26 (1953).
Brodie, D. et al., J. Am. Pharm. Assoc., 40, pp. 414–416 (1951).
Brune, K. et al., Gen. Pharmacol. 7, pp. 27–33 (1976).
Brune, K. et al., Br. J. Clin. Pharm., 10, pp. 279S–284S (1980).
Casadebaig, F. et al., Thromb. Res. 64, pp. 631–636 (1991).
Cerletti, C. et al., Biochem. Biophys, Acta., 714, pp. 122–128 (1982).
Cerletti, C., et al., Biochem. Biophys. Acta. 759, pp. 125 (1983).
Abattoni G., et al., Advances in Prostaglanin, Thromboxane and Leukotriene Research, 17, pp. 598–614 Raven Press, N.Y. (1988).

(List continued on next page.)

Primary Examiner—Gregory Hook
Attorney, Agent, or Firm—Klauber & Jackson

[57] ABSTRACT

A method of enhancing the anticoagulant effect of aspirin is disclosed, wherein salicylamide is coadministered. Salicylamide is essentially without anticoagulant effects of its own. A normal dose of salicylamide, approximately 30 mg to about 3.0 grams administered daily, or about 3 to 9 mg/kg body weight, can increase the anticoagulant effect of aspirin. This is particularly desirable in patients who are undergoing long-term anticoagulant therapy, e.g., cardiac patients.

12 Claims, 8 Drawing Sheets

OTHER PUBLICATIONS

Clissold, S., Drugs, 32 (supp. 4) pp. 8–26 (1986).
Davison, C., Salicylates: An International Symposium, 81, J. & A. Churchill Ltd. London (1963).
Dejana, E. et al., J. Clin. Invest., 68, pp. 1108–1112 (1981).
Ellenhorn, M. J., et al., J. Am. Pharm. Assoc., NS6, pp. 62–65 (1966).
Fitzgerald, G., et al., J. Clin. Invest. 71, pp. 676–688 (1983).
Fitzgerald, G., et al., J. Pharmacol. Exp. Ther., 259, pp. 1043–1049 (1991).
Flower, R. et al., The Pharmacological Basis Of Therapeutics, 6, pp. 682–728 Macmillan Publishing Company, New York (1980).
Frolich, J., et al., Advances In Prostaglandin, Thromboxan, And Leukotriene Research, 19, pp. 211–215. Raven Press Ltd., N.Y. (1989).
Fuster, V., et al., N. Engl. J. Med. 321, pp. 183–185 (1989).
Gabrielsson, J., et al., Life Sci., 37, pp. 2275–2282 (1985).
Gaetano, G., et al., Circulation, 72, pp. 1185–1193 (1985).
Gatti, G., et al., Int. J. Clin. Pharmacol. Res. IX(6), pp. 385–389 (1989).
Gilman, A. G. ed., et al., Goodman And Gilman's The Pharmacological Basis Of Therapeutics 6th ed. Macmillan Pub., Co., N.Y. pp. 682–728 (1980).
Goldblatt, M., J. Soc. Chem. Ind. Lond., 52, pp. 1056–1057 (1935).
Graf, P. et al., Experientia, 31, pp. 951–953 (1975).
Graham, B., et al., Clin. Pharm. Ther., 22, pp. 410–420 (1977).
Hamberg, M., et al., Proc. Natl. Acad. Sci USA., 72, pp. 2994–2998 (1975).
Harrison, L., et al., J. Pharm. Sci., 69, pp. 1268 (1980).
Hart, E. R. J. Pharmacol. Exp. Ther., 89, pp. 205–209 (1947).
Hatori, A., et al., Eur. J. Drug Metab. Pharmacokinet, 9, pp. 205–214 (1984).
Hawkins, D., et al., Science, 160, pp. 780–781 (1968).
Hennekens, C., et al., Circulation, 80, pp. 749–756 (1989).
Hogden, C., et al., J. Pharmacol. Exp. Ther., 125, pp. 275–281 (1959).
Houston, J. B., et al., J. Pharmacol. Exp. Ther., 198, pp. 284–294 (1976).
Humes J., et al., Proc. Natl. Acad. Sci. USA. 78, pp. 2053–2061 (1981).
Iwamoto, K., et al., Biochem. Pharmacol., 35, pp. 687–689 (1983).
Iwamoto, K., et al., Biochem. Pharmacol., 33, pp. 3089–3095 (1984).
Koike, M., et al., J. Pharm. Sci., 70, pp. 308–311 (1981).
Kulmacz, R., et al., Mol. Pharmacol., 40, pp. 833–837 (1991).
Lasagna, L., Am. J. Med. Sci. 242, pp. 620–627 (1961).
Lefort, J., et al., Br. J. Pharmacol., 63, pp. 35–42 (1978).
Leonards, J. Proc Exp Biol. Med., 110, pp. 304–307 (1962).
Leonards, J. Clin. Pharmacol. Ther., 4, pp. 476–479 (1963).
Levy, G., Pediatrics, 62, pp. 867–872 (1978).
Levy, G., Br. J. Clin. Pharmacol., 10, pp. 285S–290S (1980).
Levy, G., J. Pharmacol. Exp. Ther., 54, pp. 1121–1125 (1965).
Levy, G. J. Pharmacol. Exp. Ther., 156, pp. 285–293 (1967).
Levy, G., J. Pharm. Sci., 57, pp. 1330–1335 (1968).
Levy, G., et al., J. Pharm. Sci., 60, pp. 608–611 (1971).
Lim, R. K., J. Pharmacol., 101, pp. 119–124 (1951).
Mahoney, C., Am. J. Cardiol, 64, pp. 387–389 (1989).
Marcus, A., N. Engl. J. Med., 297, p. 1284 (1977).
Martin, B. Advances in Pharmaceutical Sciences, 3, pp. 107–171, Academic Press, London (1971).
Mays, D., et al., J. Chromatogr. 311, pp. 310–309 (1984).
Merino, J., et al., Biochem. Pharmacol., 29, pp. 1093–1096 (1980).
Mikhailidis, D., et al., Pharmacotherapeutica, 4, pp. 255–1258 (1985).
Milne, M., Salicylates, An International Symposium 6–27 J. & A., Churchill Ltd., London (1963).
Moncada, S., et al., Nature, 263, pp. 663–665 (1976).
Morgan, A., et al., J. Pharm. Sci., 54, pp. 1640–1646 (1965).
Morris, M., et al., J. Pharm. Sci., 72, pp. 612–617 (1983).
Nelson, J., et al., J. Pharmacol. Exp. Ther., 153, pp. 159–166 (1966).

(List continued on next page.)

OTHER PUBLICATIONS

Pang, S., et al., J. Chromatogr., 420, pp. 313–327 (1987).
Patel., D., et al., Xenobiotica, 20, pp. 847–854 (1990).
Pederson, A., et al., N. Engl. J. Med., 331, pp. 1206–1211 (1984).
Peng, G., et al., J. Parm Sci., 67, pp. 710–712 (1978).
Pickard, R., et al., Nature, 219, pp. 68–69 (1968).
Quick, A. J., et al., J. Parmacol. Exp. Ther., 128, pp. 95–98 (1960).
Rainsford, K., et al., Biochem. Pharmacol., 32, pp. 1301–1308 (1983).
Rao, G., Prostaglandins Leukotriene Med., 30, pp. 133–145 (1987).
Riegelman, S., et al., J. Pharmacokinet. Biopharm., 1, pp. 419–434 (1973).
Roth, G., et al., J. Biol. Chem., 253, pp. 3782–3784 (1978).
Roth, G., et al., J. Clin. Invest., 56, pp. 624–632 (10975).
Rotilio, D., et al., Eur. J. Pharmacol., 97, pp. 197–208 (1984).
Rowland, M., et al., J. Pharm. Sci., 56, pp. 717–720 (1967).
Rowland, M. et al., J. Pharm. Sci., 61, pp. 379–385 (1972).
Rubin, G., et al., J. Pharm. Pharmacol., 35, pp. 115–117 (1983).
Rumble. R. H., et al., J. Chromatogr., 225, pp. 252–260 (1981).
Sagone, A., Jr., et al., J. Immunol., 138, pp. 2177–2183 (1987).
Schanker, L., et al., J. Pharmacol., Exp. Ther., 123, pp. 81–88 (1958).
Schreiber, T., Drugs, 38, pp. 180–184 (1989).
Seeberg, V., et al., J. Pharmacol. Exp. Ther., 101, pp. 275–282 (1951).
Seymour, R. A., Br. J. Clin. Pharmacol., 17, pp. 161–163 (1984).
Shibasaki, J., et al., J. Pharmacobiodyn., 4, pp. 91–100 (1981).
Shibasaki, J., et al., J. Pharmacobiodyn., 7, pp. 804–810 (1984).
Siegel, M., et al., Proc. Nat. Acad. Sci. USA., 76, pp. 3774–3779 (1979).
Smith B., et al., Chem. Biol. Interactions, 79, pp. 245–264 (1991).
Smith J., et al., Nature, 231, pp. 235–237 (1971).
Soldatos, C., et al., Pharmacol. 16, pp. 193–198 (1978).
Steering Committee of the "U.S. Physicians' Health Study" Research Group Final report on the aspirin component of the ongoing physicians health study, N. Engl. J. Med., 321, pp. 129–135 (1989).
Tayor, F., FDA Consumer, 14, pp. 13–16 (1980–1981).
Theroux, M., et al., N. Engl. J. Med., 319, pp. 1105–1111, (1988).
Vane, J., Nature, 231, pp. 232–235 (1971).
Vargaftig, B., J. Pharm. Pharmacol., 30, pp. 101–104 (1978a).
Vargaftig, B., Eur. J. Pharmacol., 50, pp. 321–241 (1978b).
Von Euler, U., Nauny Schmiedebergs Archiv fur Experimentelle Pathologie und Pharmakologie, 175, p. 78–84 (1934).
Wallenstein, S., et al., Federation Proc., 13, pp. 414 (1954).
Wan S., et al., J. Pharm. Sci., 61, pp. 1284–1287 (1972).
Waschek, J., et al., J. Pharmacokinet Biopharm., 16, pp. 151–159 (1988).
Way, E., et al., J. Pharmacol. Exp. Ther., 108, pp. 450–460 (1953).
Wegmann, V., Schweiz, Med. Wochemschr., 80, pp. 62–63 (1950).
White, H., et al., Prostaglandine, 35, pp. 939–944 (1988).
Weiland, O., Med Klin., 44, pp. 1530–1533 (1950).
Wientjes, M., et al., J. Pharmacol., Exp. Ther., 245, pp. 809–815 (1988).
Williams, F., Clin. Pharmacokinet, 10, pp. 392–403 (1985).
Wilson, J. et al., Ther. Drug Monit., 4, pp. 147–180 (1982).
Wood, P., Salicylates: An International Symposium, 194–198 J & A Churchill Ltd., London (1963).
Zawidzka, Z., Experientia, 28(12), pp. 1482–1483 (1972).

METHOD OF ENHANCING THE ANTICOAGULANT EFFECTS OF ASPIRIN USING SALICYLAMIDE

This application is a continuation of application Ser. No. 07/977,897, filed Nov. 18, 1992, now abandoned.

The invention described herein relates to the enhancement of the anticoagulant effects of aspirin. Aspirin, or acetylsalicylic acid (ASA) has been used for years as an analgesic, antipyretic and anti-inflammatory compound. More recently, it has been used as an anticoagulant, alone as well as in combination with other agents. It has likewise been recognized that the anticoagulant effect of ASA diminishes somewhat over time.

The metabolites of ASA have been studied extensively. Unfortunately, these studies have not adequately explained the reduction in anticoagulant effect of ASA, even at steady state serum levels, which are typically observed. For example, the major ASA metabolites which have been characterized include salicylic acid, gentisic acid, salicyluric acid, salicylic acid (phenolic) glucuronide and salicylic acid (acyl) glucuronide. The presence of these compounds in the serum does not adequately explain the reduction in ASA anticoagulant activity over time.

Orally administered aspirin is rapidly and usually completely absorbed from the stomach and the upper small intestine. Absorbed aspirin is typically in its non-hydrolyzed, lipophilic unionized form. It follows first-order kinetics in man, with about 68% reaching the peripheral circulation intact. There is considerable variation in the reported absorption half-life of aspirin ranging from about four or five minutes to about 16 minutes. The rate of absorption was found to be greatly affected by the type of orally administered formulation.

Until recently, it was believed that the apparently longer elimination half life of orally administered high-dose aspirin was an artifact due to continuing drug absorption. Aspirin is rapidly hydrolyzed in the intestinal mucosa, prehepatic portal blood and liver by carboxyl esterase, to form salicylic acid. This accounts for a decrease in the bioavailability of aspirin in humans, to around 50%–70%, in spite of its complete and rapid absorption in the unhydrolyzed form.

Salicylic acid, is itself further metabolized in the liver to salicyluric acid, salicyl phenol glucuronide, salicyl acyl glucuronide, gentisic acid and 2,3-dihydroxybenzoic acid. Metabolism of aspirin also takes place in other tissues, e.g., kidney. While the formation of salicyl phenol glucuronide and salicyluric acid follow zero-order kinetics, other metabolites follow first-order kinetics after the administration of therapeutic doses.

In other species, e.g., rats, aspirin undergoes an extensive first-pass effect when administered orally. More than 60% of the oral dose of aspirin undergoes intestinal and hepatic extraction and/or metabolism during passage through the intestine and liver. The pharmacokinetics of salicylic acid were found to be non-linear and dose-dependent in both humans and rats. Salicylate was also found to exhibit a concentration-dependent distribution and plasma albumin binding.

Salicylamide is the amide derivative of salicylic acid and is not hydrolyzed in vivo to form a salicylate. This is contrary to aspirin and related compounds. Hence, salicylamide is not considered to be a true salicylate pharmacologically. Salicylamide does not possess anticoagulant activity on its own. It has been effectively used as an analgesic, antipyretic, anti-inflammatory and hypnotic. The compound is readily absorbed from the gastrointestinal tract and undergoes pronounced first-pass metabolism, up to about 70% of the administered dose. It is primarily metabolized by the liver into salicylamide glucuronide, salicylamide sulfate and gentisamide. The compound gentisamide is further metabolized to the glucuronide and sulfate.

Gentisamide is presently believed to be the only pharmacologically active metabolite of salicylamide. About 50% of the level of salicylamide is bound to plasma proteins. The plasma and tissue concentrations of salicylamide fall rapidly due to renal excretion, whereas biliary excretion is negligible.

Salicylamide has been used in combination with aspirin for its analgesic and anti-inflammatory effects. However, the combination has not previously been used for the aspirin anticoagulant-enhancing effect of the salicylamide.

Consequently, one object of the present invention is to provide a method of counteracting the normal reduction of ASA anticoagulant activity which is typically observed.

Another object of the present invention is to extend or prolong the anticoagulant effect of ASA which is seen over time, without resort to increasing the dose of ASA which is administered, or increasing the dosage frequency.

Another object of the present invention is to provide a prolonged anticoagulant effect without increasing the side effects which can occur with aspirin, and without increasing the risk of excessive or uncontrollable bleeding which may occur with the use of other anticoagulants.

These and other objects will be apparent to those of ordinary skill from the teachings herein.

PUBLICATIONS

The following publications contain background information and procedural materials which can be used in connection with the invention. Each of the publications is hereby incorporated by reference.

Abdel-Rahman, M. et al. "Bioavailability of aspirin and salicylamide following oral co-administration in human volunteers." *Can. J. Physiol. Pharmacol.* 69:1436–1442 (1991) relates to the levels of aspirin and salicylamide following oral administration. No description of the enhanced anticoagulant effect of aspirin in the presence of salicylamide is provided.

The references noted below are provided as being of general interest:

Ali, M. et al. "Interference by sulphinpyrazone and salicylate of aspirin inhibition of platelet cyclooxygenase activity." *Prostaglandin Med.* 3:327–332 (1979).

Al-Mondhiry, H. et al. "On the mechanism of platelet function inhibition by acetylsalicylic acid." *Proc. Soc. Exp. Biol. Med.* 133:632–636 (1970).

Austen, K. "The role of arachidonic acid metabolites in local and systemic inflammatory processes." *Drugs* 33 (supp.) 10–17 (1987).

Bakar, S. K., et al., "Determination of Salicylamide and five metabolites in biological fluids by high-performance liquid chromatography." *J. Pharm. Sci.,* 72:1020–1023 (1983).

Barr, W. et al. "Intestinal drug metabolism-presystemic and systemic mechanisms and implications therein." in Benet et al. (Eds.) *Pharmacokinetics, A Modern View* 426–429 Plenum Press, New York (1969).

Barr, W. "Factors involved in the assessment of systemic or biologic availability of drug products." *Drug Inf. Bull.* 27–45 (Jan./June 1969).

Barr, W., et al. "Dose dependent drug metabolism during the absorptive phase." *Rev. Can. Biol.* 32 (supp.) 31–42 (1973).

Batterman, R. et al. "Effectiveness of salicylamide as analgesic and antirheumatic agent." *J. Am. Med. Assoc.* 159:1619–1622 (1955).

Baven, E., et al. "The analgesic and antipyretic properties of some derivatives of salicylamide." *J. Pharm. Pharmacol.* 6:872–878 (1952).

Berger, F. "Hypnotic action resulting from combined administration of salicylamide and acetophenetidin." *Proc. Soc. Exp. Biol. Med.* 87:449–451 (1954).

Borovsky, M. "Antipyretic activity of acetylsalicylic acid and salicylamide suspension in pediatrics." *Am. J. Dis. Child.* 100:23–30 (1960).

Brandon, R., et al. "A sensitive liquid chromatographic assay for plasma aspirin and salicylate concentration after low doses of aspirin." *Ther. Drug Monit.* 7:216–221 (1985).

Braden, G., et al. "Suppression of eicosanoid formation during coronary angioplasty by fish oil and aspirin." *Circulation* 84:679–685 (supp.) (1991).

Brecher, G., et al. "The reproducibility and constancy of the platelet count." *Am. J. Clin. Path.* 23:15–26 (1953).

Brodie, D., et al. "A note on hydrolysis of salicylamide." *J. Am. Pharm. Assoc.* 40:414–416 (1951).

Brune, K., et al. "Mechanisms of action of anti-inflammatory drugs." *Gen. Pharmacol.* 7:27–33 (1976).

Brune, K., et al. "Biodistribution of mild analgesics." *Br. J. Clin. Pharm.* 10:279S–284S (1980).

Casadebaig, F., et al. "Action of some salicylate derivatives on in vitro platelet aggregation. Inhibitory and inhibition antagonistic effects." *Thromb. Res.* 64:631–636 (1991).

Cerletti, C., et al. "Non-steroidal anti-inflammatory drugs react with two sites on platelet cyclooxygenase: evidence from in vivo drug interaction studies in rats." *Biochem. Biophys. Acta.* 714:122–128 (1982).

Cerletti, C., et al. "Salicylates fail to prevent the inhibitory effect of 5,8,11,14-eicosatetraynoic acid on human platelet cyclooxygenase and lipooxygenase activities." *Biochem. Biophys. Acta.* 759:125 (1983).

Ciabattoni, G., et al. "Radioimmunoassay measurement of 2,3-dinor metabolites of prostacyclin and thromboxane in human urine." In Samuelsson et al. (Eds.) *Advances in Prostaglandin, Thromboxane and Leukotriene Research* 17:598–614 Raven Press, New York (1988).

Clissold, S. "Aspirin and related derivatives of salicylic acid." *Drugs* 32 (supp. 4) 8–26 (1986).

Davison, C. "Protein Binding of Salicylates." by Stafford. In Dixon et al. (Eds.) *Salicylates: An International Symposium* 81 J. & A. Churchill Ltd., London (1963).

Dejana, E., et al. "Salicylate-aspirin interaction in the rat." *J. Clin. Invest.* 68:1108–1112 (1981).

Ellenhorn, M. J., et al., "Clinical look at problems of drug interactions." *J. Am. Pharm. Assoc.,* NS6:62–65 (1966).

Fitzgerald, G., et al. "Endogenous synthesis of prostacyclin and thromboxane and platelet function during chronic aspirin administration in man." *J. Clin. Invest.* 71:676–688 (1983).

Fitzgerald, G., et al. "Presystemic acetylation of platelets by aspirin: reduction in rate of drug delivery to improve biochemical selectivity for thromboxane $A_2$." *J. Pharmacol. Exp. Ther.* 259:1043–1049 (1991).

Flower, R., et al. "Analgesic-antipyretics and anti-inflammatory agents: drugs employed in the treatment of gout." in Goodman and Gilman (Eds) *The Pharmacological Basis of Therapeutics* 6:682–728 Macmillan Publishing Company, New York (1980).

Frölich, J., et al. "Role of eicosanoids in regulation of vascular resistance." In Samuelsson et al. (Eds) *Advances in Prostaglandin, Thromboxane, and Leukotriene Research* 19:211–215 Raven Press Ltd., New York (1989).

Fuster, V., et al. "Aspirin in the prevention of coronary disease." *N. Engl. J. Med.* 321:183–185 (1989).

Gabrielsson, J., et al. "Constant rate of infusion improvement of tests for teratogenicity and embryotoxicity." *Life Sci.* 37:2275–2282 (1985).

Gaetano, G., et al. "Pharmacology of platelet inhibition in humans: implications of the salicylate-aspirin interaction." *Circulation* 72:1185–1193 (1985).

Gatti, G., et al. "Pharmacokinetics of salicylic acid following administration of aspirin tablets and three different forms of soluble aspirin in normal subjects." *Int. J. Clin. Pharmacol. Res IX*(6). 385–389 (1989).

Gilman, A. G. ed, et al., "Analgesic-antipyretics and anti-inflammatory agents; drugs employed in the treatment of gout." In *Goodman and Gilman's The Pharmacological Basis of Therapeutics* 6th ed. Macmillan Pub. Co., N.4, pp 682–728 (1980).

Goldblatt, M. "A depressor substance in seminal fluid." *J. Soc. Chem. Ind. Lond.* 52:1056–1057 (1935).

Graf, P., et al. "Acidic non-steroidal anti-inflammatory drugs accumulating in inflamed tissues." *Experientia* 31:951–953 (1975).

Graham, G., et al. "Patterns of plasma concentrations and urinary excretion of salicylate in rheumatoid arthritis." *Clin. Pharm. Ther.* 22:410–420 (1977).

Hamberg, M., et al. "Thromboxanes: a new group of biologically active compounds derived from prostaglandin endoperoxide." *Proc. Natl. Acad. Sci. USA* 72:2994–2998 (1975).

Harrison, L., et al. "High-pressure liquid chromatographic determination of salicylsalicylic acid, aspirin, and salicylic acid in human plasma and urine." *J. Pharm. Sci.* 69:1268 (1980).

Hart, E. R., "Toxicity and analgesic potency of salicylamide and certain of its derivatives as compared with established analgesic antipyretic drugs." *J. Pharmacol. Exp. Ther.,* 89:205–209 (1947).

Hatori, A., et al. "The metabolism of aspirin in rats: localization, absorption, distribution and excretion." *Eur. J. Drug Metab. Pharmacokinet.* 9:205–214 (1984).

Hawkins, D., et al. "Acetylation of human serum albumin by acetylsalicylic acid." *Science* 160:780–781 (1968).

Hennekens, C., et al. "Aspirin and other antiplatelet agents for the secondary and primary prevention of heart disease." *Circulation* 80:749–756 (1989).

Hogden, C., et al. "Absorption of drugs from the stomach in the human." *J. Pharmacol. Exp. Ther.* 120:540–545 (1957).

Hogden, C., et al. "On the mechanism of intestinal absorption of drugs." *J. Pharmacol. Exp. Ther.* 125:275–281 (1959).

Houston, J. B., et al. "Effect of route of administration on competitive drug biotransformation interaction:

salicylamide-ascorbic acid interaction in rats." *J. Pharmacol. Exp. Ther.* 198:284–294 (1976).

Humes, J., et al. "Multiple sites on prostaglandin cyclooxygenase are determinants in the action of non-steroidal anti-inflammatory agents." *Proc. Natl. Acad. Sci. USA* 78:2053–2061 (1981).

Iwamoto, K., et al. "Gastrointestinal and hepatic first pass metabolism of aspirin in rats." *J. Pharm. Pharmacol.* 35:687–689 (1983).

Iwamoto, K., et al. "Gastrointestinal and hepatic first-pass effects of salicylamide in rats." *Biochem. Pharmacol.* 35:687–689 (1983).

Iwamoto, K., et al. "Difference in hepatic uptake kinetics of aspirin and salicylamide in rats." *Biochem. Pharmacol.* 33:3089–3095 (1984).

Koike, M., et al. "Sulfoconjugation and glucuronidation of salicylamide in isolated rat hepatocytes." *J. Pharm. Sci.* 70:308–311 (1981).

Kulmacz, R., et al. "Prostaglandin H synthase: perturbation of the tyrosyl radical as a probe of anticyclooxygenase agents." *Mol. Pharmacol.* 40:833–837 (1991).

Lasagna, L. "Analgesic drugs". *Am. J. Med. Sci.*, 242"620–627 (1961).

Lefort, J., et al. "Role of platelets in aspirin-sensitive bronchoconstriction in guinea pig; interactions with salicylic acid. *Br. J. Pharmacol.* 63:35–42 (1978).

Leonards, J. "Presence of acetylsalicylic acid in plasma following oral ingestion of aspirin." *Proc. Exp. Biol. Med.* 110:304–307 (1962).

Leonards, J. "The influence of solubility on the rate of gastrointestinal absorption of aspirin." *Clin. Pharmacol. Ther.* 4:476–479 (1963).

Levy, G. "Clinical pharmacokinetics of aspirin." *Pediatrics* 62:867–872 (1978).

Levy, G. "Clinical pharmacokinetics of salicylates: a reassessment." *Br. J. Clin. Pharmacol.* 10:285S–290S (1980).

Levy, G., et al. "Dissolution rate-limited absorption in man." *J. Pharmacol. Exp. Ther.* 54:1121–1125 (1965).

Levy, G., et al. "Pharmacokinetics of salicylamide elimination in man." *J. Pharmacol. Exp. Ther.* 156:285–293 (1967).

Levy, G., et al. "Drug biotransformation interaction in man. I. Mutual inhibition in glucuronide formation of salicylic acid and salicylamide in man." *J. Pharm. Sci.* 57:1330–1335 (1968).

Levy, G., et al. "Drug biotransformation interaction in man. V. Acetaminophen and salicylic acid." *J. Pharm. Sci.* 60:608–611 (1971).

Lim, R. K., "Salicylate analgesia." In *The Salicylates*. Ed by Smith, M. J. H. et al, Interscience Pub. N.Y., pp. 155–202 (1966).

Litter, M., et al. "Salicylamide: pharmacology, fate, and clinical use." *J. Pharmacol.* 101:119–124 (1951).

Mahony, C. "Effect of aspirin on myocardial ischemia." *Am. J. Cardiol.* 64:387–389 (1989).

Marcus, A. "Aspirin and thromboembolism: a possible dilemma." *N. Engl. J. Med.* 297:1284 (1977).

Martin, B. "The formulation of aspirin." in Bean et al. (Eds) *Advances in Pharmaceutical Sciences* 3:107–171 Academic Press, London (1971).

Mays, D., et al. "Improved method for the determination of aspirin and its metabolites in biological fluids by high-performance liquid chromatography: applications to human and animal studies." *J. Chromatogr.* 311:301–309 (1984).

Merino, J., et al. "Salicylate reverses in vitro aspirin inhibition of rat platelet and vascular prostaglandin generation." *Biochem. Pharmacol.* 29:1093–1096 (1980).

Mikhailidis, D., et al. "The effect of diflunisal administration on platelet aggregation and cerebral blood flow." *Pharmacotherapeutica* 4:255–258 (1985).

Milne, M. "The excretion of salicylate and its metabolites." in Dixon et al. (Eds) *Salicylates, An International Symposium* 6–27 J. & A. Churchill Ltd., London (1963).

Moncada, S., et al. "An enzyme isolated from arteries transforms prostaglandin endoperoxide to an unstable substance that inhibits platelet aggregation." *Nature* 263:663–665 (1976).

Morgan, A., et al. "Evaluation of acetyl-salicylic acid esterase in aspirin metabolism." *J. Pharm. Sci.* 54:1640–1646 (1965).

Morris, M., et al. "Determination of salicylamide and five metabolites in biological fluids by high-performance liquid chromatography." *J. Pharm. Sci.* 72:612–617 (1983).

Nelson, J., et al. "Comparative pharmacokinetics of salicylate elimination in men and rats." *J. Pharmacol. Exp. Ther.* 153:159–166 (1966).

Pang, S., et al. "High-performance liquid chromatographic method for the quantitation of salicylamide and its metabolites in biological fluids." *J. Chromatogr.* 420:313–327 (1987).

Patel, D., et al. "Comparative metabolism of high doses of aspirin in man and rat." *Xenobiotica* 20:847–854 (1990).

Pederson, A., et al. "Dose-related kinetics of aspirin. Presystemic acetylation of platelet cyclooxygenase." *N. Engl. J. Med.* 311:1206–1211 (1984).

Peng, G., et al. "Simple and rapid high-pressure liquid chromatographic simultaneous determination of aspirin, salicylic acid, and salicyluric acid in plasma." *J. Pharm. Sci.* 67:710–712 (1978).

Pinckard, R., et al. "In vitro acetylation of plasma proteins, enzymes, and DNA by aspirin." *Nature* 219:68–69 (1968).

Quick, A. J. et al, "Influence of acetylsalicylic acid and Salicylamide on the coagulation of blood." *J. Pharmacol. Exp. Ther.*, 128:95–99 (1960).

Rainsford, K., et al. "Distribution of the acetyl compared with the salicyl moiety of acetylsalicylic acid." *Biochem. Pharmacol.* 32:1301–1308 (1983).

Rao, G. "Influence of anti-platelet drugs on platelet-vessel wall interactions." *Prostaglandins Leukotriene Med.* 30:133–145 (1987).

Riegelman, S., et al. "Effect of route of administration on drug disposition." *J. Pharmacokinet. Biopharm.* 1:419–434 (1973).

Roth, G., et al, "Acetylation of the $NH_2$-terminal serine of prostaglandin synthetase by aspirin." *J. Biol. Chem.*, 253:3782–3784 (1978).

Roth, G., et al. "The mechanism of the effect of aspirin on human platelets. I. Acetylation of a particulate fraction protein." *J. Clin. Invest.* 56:624–632 (1975).

Roth, G., et al. "Acetylation of prostaglandin synthetase by aspirin." *Proc. Natl. Acad. Sci. USA* 2:3073–3076 (1978).

Rotilio, D., et al. "Structural requirements for preventing the aspirin- and the arachidonate-induced inactivation of platelet cyclooxygenase: Additional evidence for distinct enzymatic sites." *Eur. J. Pharmacol.* 97:197–208 (1984).

Rowland, M., et al. "Determination of acetylsalicylic acid and salicylic acid in plasma." *J. Pharm. Sci.* 56:717–720 (1967).

Rowland, M., et al. "Absorption kinetics of aspirin in man following oral administration in an aqueous solution." *J. Pharm. Sci.* 61:379–385 (1972).

Rubin, G., et al. "Concentration-dependence of salicylate distribution." *J. Pharm. Pharmacol.* 35:115–117 (1983).

Rumble, R. H., et al. "Determination of aspirin and its major metabolites in plasma by high performance liquid chromatography without solvent extraction." *J. Chromatogr.* 225:252–260 (1981).

Sagone, A., Jr., et al. "Oxidation of salicylates by stimulated granulocytes: evidence that these drugs act as free radical scavengers in biological systems." *J. Immunol.* 138:2177–2183 (1987).

Schanker, L., et al. "Absorption of drugs from the rat small intestine." *J. Pharmacol. Exp. Ther.* 123:81–88 (1958).

Schreiber, T. "Aspirin and thrombolytic therapy for acute myocardial infarction." *Drugs* 38:180–184 (1989).

Seeberg, V., et al. "Absorption and distribution of salicylamide." *J. Pharmacol. Exp. Ther.* 101:275–282 (1951).

Seymour, R. A., "The efficacy and pharmotunetics of Sodium salicylate in post-operative dental pain." *Br. J. Clin. Pharmacol.* 17:161–163 (1984)

Shibasaki, J., et al. "Some quantitative evaluation of first-pass metabolism of salicylamide in rabbit and rat." *J. Pharmacobiodyn.* 4:91–100 (1981).

Shibasaki, J., et al. "Comparison of the first-pass metabolism of ethenzamide and salicylamide in rats." *J. Pharmacobiodyn.* 7:804–810 (1984).

Siegel, M., et al. "Aspirin-like drugs interfere with arachidonic metabolism by inhibition of the 12-hydroperoxy-5,8,10,14-eicosatetraenoic acid peroxidase activity of the lipooxygenase pathway." *Proc. Natl. Acad. Sci. USA* 76:3774–3779 (1979).

Smith, B., et al. "Bioactivation of xenobiotics by prostaglandin H synthase." *Chem. Biol. Interactions* 79:245–264 (1991).

Smith, J., et al. "Aspirin selectively inhibits prostaglandin production in human platelets." *Nature* 231:235–237 (1971).

Soldatos, C., et al. "Hypnotic effectiveness of sodium salicylamide with short-term use: sleep laboratory study." *Pharmacol.* 16:193–198 (1978).

Steering Committee of the "US Physicians' Health Study" Research Group "Final report on the aspirin component of the ongoing physicians health study." *N. Engl. J. Med.* 321:129–135 (1989).

Taylor, F. "Aspirin: America's favourite drug." *FDA Consumer* 14:13–16 (1980–81).

Theroux, M., et al. "Aspirin, Heparin, or both to treat acute unstable angina." *N. Engl. J. Med.* 319:1105–1111 (1988).

Vane, J. "Inhibition of prostaglandin synthesis as a mechanism of action for aspirin-like drugs." *Nature* 231:232–235 (1971).

Vargaftig, B. "Salicylic acid fails to inhibit generation of thromboxane A$_2$ activity in platelets after in vivo administration to the rat." *J. Pharm. Pharmacol.* 30:101–104 (1978a).

Vargaftig, B. "The inhibition of cyclo-oxygenase of rabbit platelets by aspirin is prevented by salicylic acid and by phenanthrolines." *Eur. J. Pharmacol.* 50:231–241 (1978b).

von Euler, U. "Zur Kenntnis der pharmakologischen Wirkungen von Nativeskreten und Extrakten männlicher accessorischer Geβlechtsdrüsen." *Naunyn-Schmiedebergs Archiv fur Experimentelle Pathologie und Pharmakologie* 75:78–84 (1934).

Wallenstein, S., et al. "Clinical comparison of analgesic effectiveness of N-acetyl-p-aminophenol, salicylamide, and aspirin." *Federation Proc.* 13:414 (1954).

Wan, S., et al. "Renal contribution to overall metabolism of drugs II: Biotransformation of salicylic acid to salicyluric acid." *J. Pharm. Sci.* 61:1284–1287 (1972).

Waschek, J., et al. "Time-dependent, plasma-sulfate-independent kinetics of salicylamide in dogs." *J. Pharmacokinet. Biopharm.* 16:151–159 (1988).

Way, E., et al. "The toxicity and analgetic activity of some congeners of salicylamide." *J. Pharmacol. Exp. Ther.* 108:450–460 (1953).

Wegman, T. "Clinical application of Salicylamide." *Schweiz. Med. Wochenschr.* 80:62–63 (1950).

White, H., et al. "Inhibition of lyso-PAF: acetyl-CoA acetyltransferase by salicylates and other compounds." *Prostaglandins* 35:939–944 (1988).

Wieland O. "Different therapeutic uses of salicylamide. *Med. Klin.* 44:1530–1533 (1950).

Wientjes, M., et al. "Non-linear pharmacokinetics of aspirin in rats." *J. Pharmacol. Exp. Ther.* 245:809–815 (1988).

Williams, F. "Clinical significance of esterases in man." *Clin. Pharmacokinet.* 10:392–403 (1985).

Wilson, J., et al. "Efficiency, disposition and pharmacodynamics of aspirin, acetaminophen and choline salicylate in young febrile children." *Ther. Drug Monit.* 4:147–180 (1982).

Wood, P. "Studies of occult bleeding caused by salicylates and related compounds." Dixon et al. (Eds) *Salicylates: An International Symposium* 194–198 J. & A. Churchill Ltd., London (1963).

Zawidzka, Z. "Effect of Nonnarcotic analgesic on anticoagulant-induced hypoprothrombinemia in rats." *Experientia* 28(12):1482–1483 (1972).

SUMMARY OF THE INVENTION

A method of enhancing the anticoagulant effect of aspirin is disclosed. A mammal is administered an anticoagulant amount of aspirin in combination with salicylamide in an amount effective to enhance the anticoagulant effect of said aspirin.

BRIEF DESCRIPTION OF THE DRAWINGS

The invention is described herein in detail in connection with the following drawings, in which.

DETAILED DESCRIPTION

Figure 1:
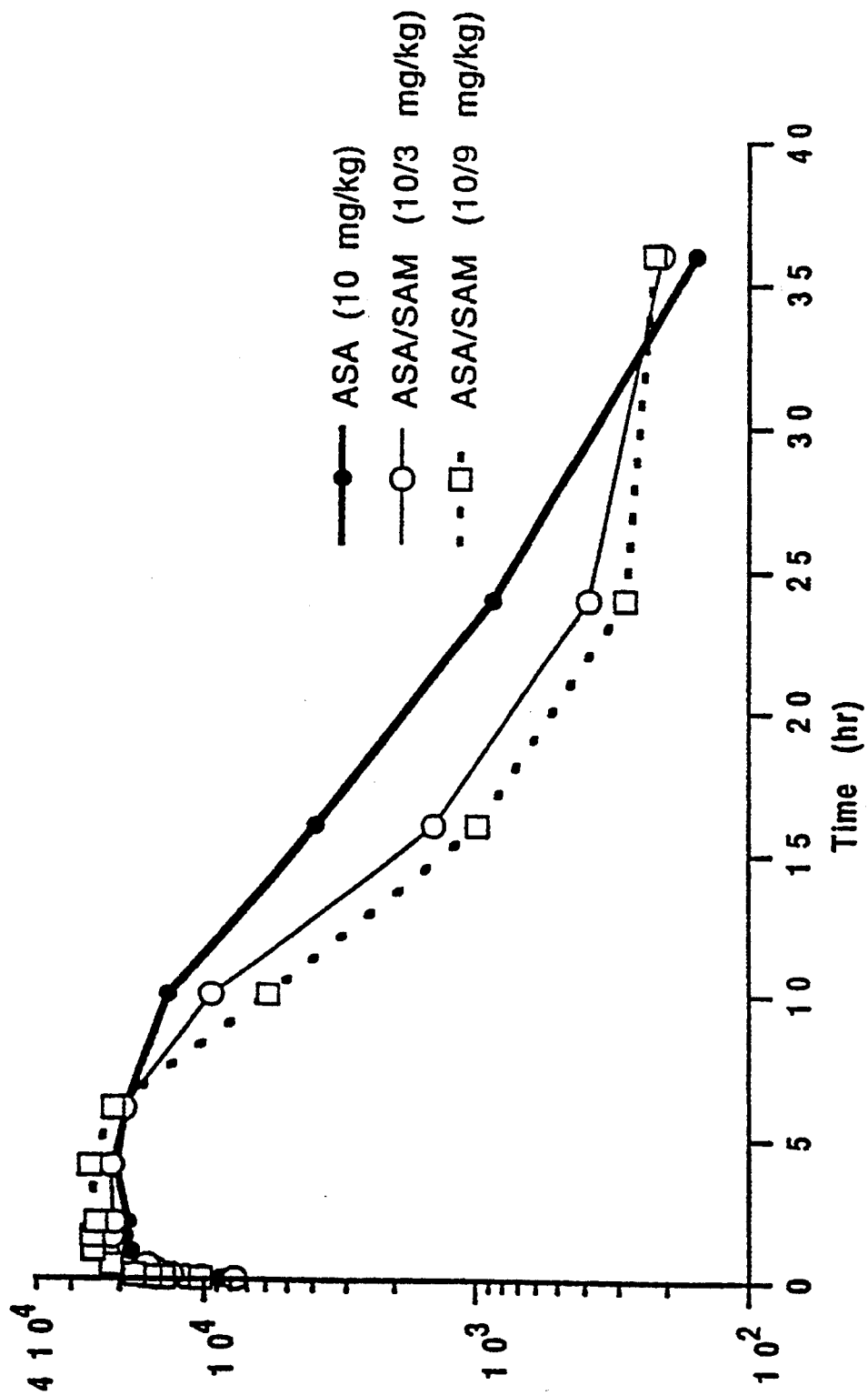
FIG. 1 is a graph of plasma time course of radioactivity following $^{14}$C-aspirin coadministration with salicylamide in low dose. Following treatment administration, blood was drawn at 2, 4, 6, 10, 20 and 30 minutes, and at 1, 1.5, 2, 4, 6, 10, 16, 24 and 36 hours. Plasma was analyzed for $^{14}$C content. The inset shows the plasma concentration over the first 4 hours. ASA= aspirin. SAM=salicylamide. Data represents the mean values with n=6.

The invention described in the present application relates to a previously unrecognized property of salicylamide, namely the ability to enhance the anticoagulation effects of aspirin. This is not correlative to any of the known characteristics or properties of either aspirin or salicylamide.

As used herein the term "enhance" refers to the effect which salicylamide has upon the anticoagulant effect of aspirin. This takes into account the length of time during which effective anticoagulation can be achieved using otherwise standard doses and serum levels of aspirin. Thus, the enhancement of anticoagulant doses of aspirin increases the length of time necessary for clotting to occur, as measured by standard clot-forming tests, such as measuring prothrombin time (PT) or partial thromboplastin time (PTT). This enables the dose of aspirin to be reduced, with a corresponding reduction in side effects experienced by the patient. Additionally, the dosing interval may be extended.

Coagulation disorders, as used herein, refers to any disease or condition wherein anticoagulation is desirable. For example, a patient with heart disease in whom anticoagulation is desired would be included. Likewise, a patient with a blood disease characterized by decreased clotting time would be included, as would patients having tendency to form clots abnormally, e.g., pulmony emboli. Thus, the term broadly encompasses any disease or condition in which clotting is a problem.

Combinations of aspirin and salicylamide have been used in the past for purposes of achieving analgesia. Each component is an analgesic in its own right. However, salicylamide has no appreciable level of anticoagulant activity on its own. It is therefore surprising that the anticoagulant effect of aspirin can or should be enhanced by salicylamide.

In humans, aspirin reaches a peak plasma concentration about 15 to 25 minutes after oral ingestion of a soluble aspirin preparation. Its concentration thereafter falls, while that of salicylic acid rises rapidly. Likewise, the apparent volume of distribution of aspirin, following absorption, is about 9.6-12.7 L/kg in adults, and about 0.12-0.14 L/kg in children.

Aspirin is typically administered to patients for its anticoagulant effects in doses which are somewhat lower than those used in the treatment of pain and inflammation. Normal daily anticoagulant doses for adults range from about 10 mg to about 1 gram.

Salicylamide is typically administered for its analgesic and/or anti-inflammatory effects in adult doses ranging from about 30 mg to about 250 mg. Due to the multiple dose nature of these products, the total daily dose in these conditions can therefore range from as low as about 30 mg to as high as about 3 grams.

As described herein in detail, the total daily dose of SAM for enhancing anticoagulation ranges from about 25 mg to about 3.0 grams. Typically, this results in administration of about 2 to 10, and preferably 3-9 mg/kg SAM per dosage administration.

The ASA/SAM combination may be fixed, so that a given amount of the combination provides a constant dosage on a percentage basis, or the drugs can be administered separately to achieve the desired effect, and enable one to vary the ratio of ASA to SAM. The compounds can be administered by any preferred route of administration, e.g., orally, rectally or parenterally, but the preferred route of administration is oral.

Any suitable oral dosage form can be used. The preferred dosage forms are tablets and capsules, either of which can be administered as often as necessary to achieve the desired anticoagulant effects, e.g., once daily, up to as many as about four to six doses per day. The preferred dosages are tablets and capsules which can be administered once daily, i.e., delayed release formulations which provide a release of active ingredient over the twenty-four hour period.

Alternatively, the use of aspirin oral solution is therapeutically favorable since it ensures prompt action with less gastric irritation due to less contact time of ASA with the gastric mucosa. The solution form was used to administer both ASA and SAM because the absorption of ASA and the bioavailability of SAM were found to be superior when oral solutions were administered rather than the solid forms (tablets or suspensions). The solution form also minimizes the variability in absorption which is encountered with solid forms and suspensions.

Without limiting the invention to a particular mechanism of action, the analgesic, anti-inflammatory and antipyretic effects of aspirin are believed to be due to the inhibition of prostaglandin synthesis, since salicylic acid does not have the capacity to inhibit cyclooxygenase. It has likewise been determined that both aspirin and salicylic acid have an inhibitory effect on lyso-PAF:acetyl-CoA acetyltransferase, an enzyme responsible for the formation of platelet activating factor. Platelet activating factor (PAF) has been determined to act as a pharmacological mediator in inflammation, pain, anaphylaxis and other disease conditions.

Aspirin and other salicylates also have been demonstrated to reversibly block the lipooxygenase pathway, which is postulated to be responsible for the anti-inflammatory effects of these compounds. Again, salicylamide is an exception. It does not have a demonstrable effect on the cyclooxygenase pathway in vitro.

Aspirin and the other salicylates have also been demonstrated to be antagonists of prostaglandins, pharmacological mediators formed by the action of cyclooxygenase on arachidonic acid (AA). Both of prostaglandins PG G2 and PG H2 are biologically active, and are further metabolized to other more stable prostaglandins, thromboxane $A_2$, prostacyclin (PG $I_2$), PG $E_2$ and PG $F_{2\alpha}$.

The pharmacokinetics of salicylic acid, aspirin and salicylamide can be demonstrated, employing a two dose regimen, using the compounds alone and in ratio combinations. Plasma concentration vs. time profiles were generated in rats, and the effect of salicylamide on the excretion of aspirin and its metabolites in rats was evaluated upon oral coadministration.

Tissue distribution evaluation is included to delineate the interaction of aspirin and salicylamide upon oral coadministration. An antagonistic effect of salicylic acid on the antiplatelet and antithrombotic effects of aspirin were noted. SAM appears to reduce the negative effects of salicylic acid. This is believed to have a salutary effect on the anticoagulant effects of aspirin against thrombosis.

Likewise, functional studies were conducted to determine whether the interaction of salicylamide and aspirin involved platelet and vascular cyclooxygenase. Salicylamide again countered the antagonistic effect that salicylic acid showed on the antiplatelet effect of aspirin, its precursor compound.

MATERIALS AND METHODS

Test Compounds $^{14}$C-(carboxyl)-ASA and $^{14}$C-(carboxyl)-SAM were obtained from New England Nuclear Co., Boston, Mass. The unlabeled aspirin and salicylamide were supplied by Block Drug Company, Inc., Jersey City, N.J. Salicylic acid was obtained from Sigma Chemical Co., St. Louis, Mo.

Animals and Care

Male adult Sprague-Dawley rats (300–325 gm) obtained from Charles River Breeding Laboratory, N. Wilmington, Mass. were quarantined for one week. All animals were identified by ear punching. Food and water were provided ad libitum. The animals were maintained on rodent lab chow diet in a controlled environment with 50% humidity and 12 hour light-/dark cycle.

EXAMPLE 1

Plasma Kinetics Study of Aspirin/Salicylamide Interaction

Two dose combinations were employed. The low dose was 10 and/or 3 mg/kg of ASA and/or SAM, respectively, while the high dose was double the low dose. These doses were approximately equal (w/w) to that in commercially available combinations, e.g., BC ® formula, when administered to humans.

Rats were divided into 2 groups; the first group consisted of 30 rats which were assigned to 5 subgroups, 6 rats each, according to the following treatment scheme:

I: received $^{14}$C-ASA (10 mg/kg)
II: received $^{14}$C-ASA/SAM (10/3 mg/kg)
III: received $^{14}$C-ASA/SAM (10/9 mg/kg)
IV: received $^{14}$C-SAM (3 mg/kg)
V: received $^{14}$C-SAM/ASA (3/10 mg/kg)

The second group consisted of 4 subgroups and were administered double the dose received by the first group (with the exception of subgroup III).

The rats were fasted overnight (~18 hr.) before administration of the treatments and were allowed water ad libitum. The drug(s) to be given were prepared fresh in the morning of the study, dissolved in 2.5 ml of deionized water and gavaged to rats.

Each rat received an amount of radioactivity equal to 1 $\mu$Ci of $^{14}$C-ASA or 1 $\mu$Ci of $^{14}$C-SAM. The specific activity of ASA was 739 and 369 dpm/$\mu$g for the low and high dose treatments, respectively. For SAM, the specific activity was 2.4 and 1.2 dpm/ng for the low and high dose treatments, respectively.

Sample Collection

Blood samples were obtained from the rats by heart puncture under ether anesthesia at 2, 4, 6, 10, 20 and 30 minutes and 1, 1.5, 2, 4, 6, 10, 16, 24 and 36 hours following treatment administration in the groups receiving $^{14}$C-ASA. In the groups receiving $^{14}$C-SAM, samples were collected until 6 hours as mentioned above, followed by a final sample at 8 hours. The samples were collected by heparinized plastic syringes and transferred to polyethylene test tubes. The samples, ~300 $\mu$l each, were rapidly centrifuged at 1800×g for 15 minutes at 4° C. The plasma was decanted and 100 $\mu$l were pipetted in scintillation vials containing 5 ml of Aquasol-2 scintillation fluid for the determination of the total plasma $^{14}$C radioactivity using Beckman LS 7500 spectrophotometer.

Calculation of the Pharmacokinetic Parameters

The pharmacokinetic parameters were evaluated for $^{14}$C following either $^{14}$C-SAM or $^{14}$C-ASA administration alone or in combination. The terminal elimination rate constant ($k_e$) was estimated by linear regression of the terminal $\beta$ phase of the plasma concentration vs. time curves. The area under the curve (AUC$\infty$) was calculated by using the trapezoidal method from zero to the last measured plasma concentration. The half-life of elimination ($t_{\frac{1}{2}\beta}$) was obtained by the equation $t_{\frac{1}{2}\beta} = 0.693/k_e$.

Total body clearance (Cl$_T$) was estimated by the equation Cl$_T$=Dose/AUC assuming a complete absorption of ASA and SAM (Iwamoto et al., 1982; Iwamoto et al., 1983). The apparent volume of distribution $V_d$ was calculated from the formula, $V_d = Cl_T/k_e$. Total plasma concentration vs. time profiles following $^{14}$C-ASA or $^{14}$-SAM were individually inspected to determine the maximal plasma concentration ($C_{max}$) for each animal studied.

EXAMPLE 2

Excretion Study: Effect of Salicylamide on Aspirin Excretion

Experimental Design

Eighteen rats were divided into 3 groups and received $^{14}C$-ASA (10 mg/kg) either alone, in combination with 3 mg/kg SAM or in combination with 9 mg/kg SAM orally. The dose of radiolabeled ASA administered was 5 µCi per rat. Rats were fasted overnight prior to the administration of the treatments.

Treatment

Rats were gavaged with the treatment solution and were immediately placed in Silverman metabolic glass chambers (Bioserv, Inc., Frenchtown, N.J.), one rat per chamber. Rats were administered water ad libitum while food was withheld until 1.5 hours following treatment administration. Urine was collected at 8, 16, 24, 48 and 72 hours. Feces were collected in preweighed clean plastic cups at 24, 48 and 72 hours after dosing. The expired air was channeled through a series of activated charcoal tubes to trap any radiolabeled compound that is excreted via the lungs and the tubes were collected at the end of the study 72 hours after dosing. Under vacuum suction, the expired air was also passed over a tube filled with 35 ml of ethanolamine/ethylene glycol monoethyl ether (1:2, v/v) to trap any expired $^{14}C$-$CO_2$ resulting from $^{14}C$-ASA metabolism.

Handling of Specimens

The urine samples were collected and the volume was measured using a 10 ml graduated glass pipette. The urine was shaken, and 100 µl of each urine sample were pipetted in a scintillation vial with 15 ml of Aquasol-2 for radioactivity assessment. The rest of the urine was stored at $-70°$ C. for later analysis of its content of salicylic acid (SA) and salicyluric acid (SUA), the major metabolites of ASA. (Data not shown).

Fecal weight was determined for each time-point collection and deionized water was added to feces in a ratio of feces:water, 1:3 (w/w). The feces were homogenized using electric homogenizer and 200 mg of the homogenate were analyzed for their content of $^{14}C$ radioactivity.

1 ml of the ethanolamine/ethylene glycol monoethyl ether was counted for its content of $^{14}C$ radioactivity. The activated charcoal was carefully emptied in small glass tubes and extracted with 1 ml of methanol and the tubes were then centrifuged at 1800×g for 15 minutes. 100 µl of the supernatant were transferred in scintillation vials containing 15 ml Aquasol-2 for the measurement of $^{14}C$ content.

Characterization of the Urinary Metabolites of ASA

Urine was further studied for its content of the ASA metabolites, namely SA and SUA. Waters HPLC system (Waters Chromatography, Division of Millipore, Milford, Mass.) with 3.9 mm×15 cm NOVA-PAK 4 µm silica packing steel column, C-18 Guard-Pak, and Milli-Q(tm) Millipore water filtration system were used for the characterization of SA and SUA. An isocratic methodology was developed and the separation was optimal by a mobile phase of 2% acetic acid/methanol, 70:30, at a flow rate of 1 ml/min. and a detection wavelength of 240 nm. One hundred µl of the collected 8 and 16 hour urine samples were diluted with 4 ml of methanol/mobile phase mixture (1:1) while the dilution was only with 2 ml for the 24, 48 and 72 hour urine samples.

The fractions under the specific retentiontimes of SA and SUA were collected in scintillation vials containing 15 ml of the scintillation cocktail and the radioactivity content was counted. The retention times of SA and SUA were determined by injection of authentic standard solution. Corrections have been made for the quenching effect of the mobile phase.

Calculation of the Urine Content of SA Glucuronides

Since other metabolites of ASA as gentisic acid and 2,3-dihydroxybenzoic acid are found in trace amounts in rat urine, the urinary content of SA glucuronide can be directly estimated by subtraction of the sum of $^{14}C$-SA and $^{14}C$-SUA from the total $^{14}C$ radioactivity in urine.

Statistical Analysis

Student-t test and one way analysis of variance (ANOVA) followed by Scheffé multiple range test were used where appropriate. The accepted level of significance of difference was $p<0.05$.

EXAMPLE 3

Study of Aspirin/Salicylamide Interaction on Tissue and Blood Plasma Distribution Experimental Design Forty-eight rats were divided into two groups. The first group of rats was administered ASA, SAM or their combination in a dose approximately equal (w/w) to that in the commercially available combinations, e.g., BC ® formula, when administered to humans, i.e., 10 and 3 mg/kg of ASA and SAM, respectively. The second group was administered double the dosage received by the first group.

Each group consisted of 24 rats and was further divided into 4 subgroups, 6 rats each, according to the following scheme:

subgroup 1: received $^{14}C$-ASA
subgroup 2: received $^{14}C$-ASA and SAM
subgroup 3: received $^{14}C$-ASA
subgroup 4: received $^{14}C$-ASA and AS Two rats were used to obtain the background values for the plasma and the tissues.

Treatment Administration

The rats were fasted overnight. The drug(s) were prepared fresh, dissolved in 2.5 ml of deionized water and administered orally by gavage needle. The rats were allowed water ad libitum before and after the oral administration.

The different treatments were given according to the previous scheme and each rat received an amount of radioactivity equal to 5 µCu in the case of radioactive aspirin and 10 µCu in the case of radioactive salicylamide. For the low and high dose ASA treatments 3696 and 1848 dpm $^{14}C$-ASA/µg total ASA were used respectively. For SAM, 24.4 and 12.2 dpm $^{14}C$-SAM/ng total SAM were utilized for low and high dose treatments, respectively.

C-Tissue Collection and Study of $^{14}C$ Radioactivity in Tissues

The rats were anesthetized by light diethyl ether inhalation. A blood sample of nearly 3 ml was collected by cardiac puncture 1.5 hours after oral administration. The blood was transferred to chilled polyethylene tubes containing 30 µl of 50% (w/w) potassium fluoride to prevent hydrolysis of ASA. A 300 µl aliquot was pipetted in a scintillation vial to study the distribution in whole blood. The rest of the collected blood was immediately centrifuged at 1800×g for 10 minutes at 4° C. and the plasma was decanted. 100 µl of the plasma were pipetted in a scintillation vial for measurement of the total radioactivity and the rest of the plasma was stored immediately at $-70°$ C. for later study of the distribution of the metabolites.

300 μl of the pellet of red blood cells was pipetted in a scintillation vial to study the distribution in red blood cells. The rest of the red blood cells were washed twice by adding 2 ml of physiological saline and were resuspended after each addition. The red blood cells were centrifuged at 3000 rpm (1800×g) for 10 minutes and 300 μl were pipetted in a scintillation vial for measurement of $^{14}C$ radioactivity.

After collecting the blood sample, the rats were sacrificed immediately by a diethyl ether overdose. The following tissues were collected: liver, lung, kidney, heart, spleen, perinephric fat, brain, upper small intestine, stomach, pancreas, bone (femur and tibia), testis, skin and skeletal muscle. A sample of bone marrow was also collected (approximately 20 mg).

300 mg tissue samples were placed in scintillation vials and 300 μl of 70% perchloric acid and 600 μl of 30% hydrogen peroxide were added to each vial and also to the vials containing the washed red blood cells aliquots. The vials were incubated at 75° C. for 1 hour in a shaking water bath and were tightly capped to prevent any loss of radioactivity by evaporation.

The vials were left to cool to room temperature for 15 minutes before 10 ml Aquasol-2 scintillation fluid was added to each vial. The total radioactivity was counted in a Beckman model 7500 LS spectrophotometer.

Liver, kidney, plasma, lung and heart were stored at −70° C. for later study of their content of the metabolites of aspirin or salicylamide using an HPLC method. Liver, kidney and plasma of the rats treated with aspirin or the combination were also investigated for the presence of salicyl glucuronide conjugates by using HPLC and acid hydrolysis assays.

Tissue samples were stored at −70° C. The tissue radioactivity content was then analyzed. (Data not shown).

Tightly Protein-Bound $^{14}C$ Radioactivity in Plasma Following $^{14}C$-ASA

The plasma tightly protein-bound activity was measured by adding 100 μl of 10% trichloroacetic acid (TCA) to 100 μl of plasma in microcentrifuge tubes and vortexing the contents for 1 minute followed by centrifugation at 1800×g for 10 minutes. The supernatant was decanted and the tubes with the pellets in them were placed in scintillation vials each containing 15 ml of Aquasol-2 scintillation fluid. A preliminary study showed no quenching effect by these transparent microcentrifuge tubes (evidenced by no increase in H number) and so eliminated the need for establishing a quench curve for the pellet content of radioactivity. The radioactivity in the scintillation vials was counted in Beckman LS counter.

Analysis of $^{14}C$-SAM in Plasma

In the case of plasma analysis, 100 μl samples were used and the remainder of the procedure was the same as described above. The pellets were not dissolved but instead directly poured in a tube containing 15 ml of the scintillation fluid and the radioactivity was measured in the Beckman LS counter.

Study of the Acid-Hydrolyzed Salicylic Acid Fraction in Plasma, Liver and Kidney of $^{14}C$-ASA-Treated Rats Since in a preliminary study, the liver, kidney and plasma were found to have the higher levels of $^{14}C$ radioactivity following $^{14}C$-ASA administration, these tissues were further studied for their content of SA glucuronides as the acid-hydrolyzed fraction of SA.

A specific HPLC method was developed for the detection of SA conjugates in plasma, liver and kidney of rats treated with $^{14}C$-ASA with or without SAM. For each sample to be analyzed, 2 aliquots each of 300 mg of tissue (liver or kidney) or 100 μl of plasma, were placed in polyethylene wide-pore tubes (Fisherbrand) along with 0.5 ml of physiological saline. The tissues were homogenized using an electrical homogenizer (Polytron, Brinkmann Instruments, Westbury, N.Y.) on high speed for 2 minutes for each sample. The tubes were dipped in ice during this procedure to minimize any loss of SA by sublimation from the heat generated by the high speed of the homogenization.

The homogenates were transferred by pipette to pyrex screw-top test tubes and the tubes were then divided into 2 groups:

To one set of tubes, 0.5 ml of 6N HCl was added and the tubes were vortexed and heated in a water bath at 100° C. for 1 hour. The temperature was checked by a thermometer to ensure no overheating of the samples. Subsequently, the tubes were left to cool to room temperature for 30 minutes before 3 ml of methanol were added to each tube. To the duplicate control tubes containing the homogenates, 0.5 ml of saline were added followed by 3 ml of methanol.

The contents of the tubes were then mixed in a mechanical shaker for 10 minutes at low speed and were subsequently centrifuged for 10 minutes at 1800×g in Beckman J-6B centrifuge.

The supernatants were filtered through disposable 0.45 μm Acrodisc filters and 100 μl were injected onto HPLC. The fraction of eluate under the peak of salicylic acid was collected over 15 ml of Aquasol-2 in glass scintillation vials. The radioactivity in the vials was measured by Beckman LS scintillation counter and the difference in radioactivity between the control vials and the acidhydrolyzed ones was indicative of SA conjugates as well as part of the protein-bound SA in the tissue samples.

HPLC Conditions

A Waters HPLC system (Waters Chromatography, Division of Millipore, Milford, Mass.) was used, consisting of: Waters 680 automated gradient controller, two model 510 pumps, model U6K universal liquid chromatography injector, Lambda Max model 481 variable wavelength UV/Vis absorbance detector, Data Module 730, 3.9 mm×15 cm NOVA-PAK 4 μm silica packing steel column, C-18 Guard-Pak, Hamilton syringes of 10, 100, and 250 μl capacity (Hamilton Co., Reno, Nev.), and Milli-Q(tm) Millipore water filtration system #CDOFO 1205 (Waters, Division of Millipore, Milford, Mass.).

Three different isocratic methodologies were developed to ensure optimal quantitation of ASA, SAM and their metabolites in tissues as follows:

1—For the analysis of ASA and its metabolites in tissues: the mobile phase was 2% acetic acid/methanol, 95:5, at a flow rate of 1.4 ml/minute.

2—For the detection of SA glucuronides: the mobile phase was 2% acetic acid/methanol, 70:30, at a flow rate of 1 ml/minute.

3—For the detection of SAM and GAM in tissues: the mobile phase was 2% acetic acid/methanol, 95:5, at a flow rate of 1.4 ml/minute.

The detection wavelength was 240 nm and the sensitivity of the detector was 0.02 AUFS (Absorbance Unit Full Scale). All the methods were validated and precision, linearity, capacity factor, resolution, and theoretical plate counts were determined to be satisfactory.

EXAMPLE 4

Aspirin/Salicylamide Interaction on Platelet and Vascular Cyclooxygenase

Platelet Count

Was done manually by the method of Brecher and Conkite (1953) using phase contrast microscopy (Balplan) with a 40×annulus, 40×phase objective, and 10×ocular (total of 400×), and a special platelet counting chamber (American Optical Corp., Buffalo, N.Y.) and dilution with 1% ammonium oxalate. The platelet-rich plasma (PRP) was adjusted by dilution with platelet-poor plasma (PPP) to give a final count of $1 \times 10^9$ platelets/ml.

Arachidonic Acid (AA) Solution

Arachidonic acid (as the sodium salt, >99.0% pure) was obtained from Sigma Chemical Co. and a stock solution of 34.5 mM was prepared by dissolving in isotonic saline. 20 μl of the stock solution were added to 440 μl of PRP (400 μl of PRP and 20 or 40 μl of treatment solution ±20 μl of saline) to make a 23 fold dilution. The final concentration of AA in PRP was 1.5 mM.

EDTA/ASA Solution

EDTA solution was prepared by adding 2 gm disodium EDTA and 0.8 gm NaCl and were adjusted to pH 7.4 with NaOH and made up to a final volume of 100 ml in distilled water. ASA solution was prepared by dissolving 30 mg in 10 ml of isotonic saline to make a solution of 3 mg/ml.

950 μl of EDTA solution were added to 50 μl of ASA solution and the mixture was vortexed. 40 μl of the mixture were pipetted in the experiment test tubes to stop further prostaglandin production.

EXAMPLE 5

Interaction of Aspirin, Salicylamide and Salicylic Acid on Thromboxane $B_2$ Synthesis by Platelet-Rich Plasma in vitro Platelet-rich plasma (PRP) was prepared from male Sprague-Dawley rats (300-325 gm). The blood was collected by heart puncture and added to 3.8% citrate solution, final volume 9:1, blood:citrate. The blood was centrifuged at 120×g (750 rpm) for 15 minutes at 4° C. to obtain PRP. The rest of the blood was spun at 1800×g (3000 rpm) for 10 minutes to get the PPP which was used later for dilution of the PRP to achieve the final desired platelet concentration of $1 \times 10^9$ platelets/ml. 400 μl of PRP, containing $4 \times 10^8$ platelets, were pipetted in polypropylene tubes and the following treatment groups were studied:

1—Baseline (−ve control) tubes: to measure the baseline production of Thromboxane $B_2$ (TX $B_2$) by platelets during the time of the experiment, 60 μl of saline were added and left for 10 minutes in a shaking water bath at 37° C.

2—Control (+ve control) tubes: 20 μl of arachidonic acid (AA) solution were added to achieve a final concentration of 1.5 mM and the tubes were incubated for minutes.

3—ASA and/or SAM treatment tubes: 20 μl of ASA (final conc. 130 μg/ml), 20 μl of SAM solution (final conc. 40 μg/ml), 20 μl of ASA/SAM(L) solution (final conc. 130/40 μg/ml) or 20 μl of ASA/SAM(H) solution (final conc. 130/120 μg/ml) were added to PRP together with 20 μl of saline for 10 minutes, then 20 μl of AA solution were added for additional 10 minutes.

4—ASA/SA treatment: 20 μl of ASA/SA solution (final conc. 130/130 μg/ml) and 20 μl of saline were added to the tubes for 10 minutes before AA was added for further 10 minutes.

5—ASA/SA/SAM treatment: 20 μl of ASA/SA solution (130/130 μg/ml as final conc.) and 20 μl of SA solution in low (L) or high (H) concentrations (40 or 120 μg/ml, final conc.) were added simultaneously to PRP followed 10 minutes later by AA.

6—SAM/SA treatment: 20 μl of SAM solution (final conc. 40 μg/ml) and 20 μl of SA solution (final conc. 130 μg/ml) were added followed 10 minutes later by AA for additional 10 minutes.

Also, the effect of SAM when administered first to the platelets followed 10 minutes later by ASA was studied to know whether the effect of SAM is time dependent or not.

During the treatment, all the tubes were incubated at 37° C. in a shaking water bath. Ten minutes after the addition of AA, or saline (for the control tubes), the experiment was ended by addition of 40 μl of EDTA/ASA solution. The tubes were immediately centrifuged at 1800×g for 15 minutes at 4° C. to precipitate the platelets and 100 μl of the supernatant were obtained for estimation of their content of TX $B_2$ using a specific radioimmunoassay (Amersham International) (vide infra).

EXAMPLE 6

Interaction of Aspirin and Salicylamide on 6-keto PG $F_{1alpha}$ Production from Thoracic Aortic Rings ex vivo The method used was a modification of that used by Dejana et al. (1981). Male Sprague-Dawley rats were randomly treated with either ASA (10 mg/kg), SAM (9 mg/kg), ASA/SAM (10/9 mg/kg), or isotonic saline. The rats were fasted overnight before administration of the treatments. Half an hour following treatment, the rats were exsanguinated by heart puncture under ether anesthesia and the thoracic aorta was immediately isolated, cleaned of adventitia, and flushed in situ with 5 ml of isotonic saline. The vessel was then removed and 2 rings (each was nearly 7 mg wet weight corresponding to 0.5 cm length) were cut from the middle part. The rings were immediately incubated in 160 μl of Krebs-Hanseleit buffer solution adjusted to pH 7.4 and containing AA (final concentration 4.3 mM) in polyethylene tubes. The tubes were incubated at 37° C. in a shaking water bath for 10 minutes. The reaction was terminated by the addition of 40 μl of EDTA/ASA solution and the tubes were centrifuged at 1800×g for 15 minutes at 4° C. 100 μl of the supernatant were used for the measurement of 6-keto PG $F_{1alpha}$ content as an indicator of its unstable precursor, PG $I_2$. A specific radioimmunoassay (Amersham International) (vide infra) was employed.

EXAMPLE 7

Radioimmunoassay Procedure for Measurement of Thromboxane $B_2$ and 6-keto PG $F_{1alpha}$ The procedure described below is for thromboxane $A_2$. A similar procedure was used for 6-keto PG $F_{1alpha}$ measurement.

Preliminary Steps

All components, except the dextran-coated charcoal, were allowed to thaw and reach room temperature before beginning the assay. The components were not refrozen after they have been thawed.

1) 12×75 mm polypropylene tubes were labeled for total count tubes (TC), non-specific binding tubes (NSB, otherwise known as the buffer blank), zero standard tub($B_0$), standards A–E and sample tubes.

2) 200 µl of vial number 1, assay buffer, were pipetted in the TC and NSB tubes.

3) 100 µl of vial number 1, assay buffer, were pipetted in the $B_0$ tubes.

| Radioimmunoassay Reagents* | | | | | |
|---|---|---|---|---|---|
| Tube | TC | NSB | $B_0$ | Standards A–E | Samples 1, 2 ... n |
| Buffer | 200 | 200 | 100 | — | — |
| ($^3$H) TX $B_2$ or ($^3$H) 6-keto PG $F_{1alpha}$ | 100 | 100 | 100 | 100 | 100 |
| Standard | — | — | — | 100 | — |
| Samples | — | — | — | — | 100 |
| Antiserum | — | — | 100 | 100 | 100 |
| Mix and incubate at room temperature for 1 hour then at 2–8° C. for 16–20 hours | | | | | |
| Charcoal suspension | — | 1 | 1 | 1 | 1 |
| React, centrifuge, decant and measure $^3$H decay | | | | | |

*The volume was in µl for all reagents except for charcoal which was in ml.

4) 100 hundred µl of vial number 2, ($^3$H) thromboxane $B_2$, were pipetted in all tubes.

5) 100 µl of each thromboxane $B_2$ standard were pipetted in the appropriately labeled tubes.

6) 100 µl of the sample to be assayed were pipetted in the appropriately labeled tubes.

7) 100 µl of vial number 3, thromboxane $B_2$ antiserum were pipetted in the $B_0$, standard, and sample tubes.

8) The contents of each tube were mixed with a vortex mixer, the tubes were centrifuged for 15 seconds at 1000×g (2250 rpm) and the contents of each tube were again mixed with a vortex mixer. The tubes were incubated at room temperature for 1 hour and then at 2°–8° C. for 16–20 hours.

Separation of Unbound Thromboxane $B_2$ or 6-keto PG $F_{1alpha}$

9) The dextran-coated charcoal was thawed and temperature equilibrated to 2°–8° C.

10) After incubation of the assay tubes at 2°–8° C. for 16–20 hours, the assay tubes were placed in crushed ice.

11) 1.0 ml of vial number 1, assay buffer, was pipetted in the total count tubes, the contents of the tubes were mixed, and the solution was decanted in 15 ml Aquasol-2. 1.5 ml water were added to the scintillation fluid (15 ml) to clear the resulting cloudiness, since water content of Aquasol-2 is less than the recommended Amersham ACS scintillation fluid. The rim of the test tube was touched onto the surface of the scintillation fluid to draw-off the last drop from the test tube.

12) The dextran-coated charcoal was transferred into a beaker containing a magnetic stirring bar and the beaker was placed in crushed ice. The dextran-coated charcoal was set on a magnetic stirrer and the stirring speed was adjusted so that the charcoal was kept in suspension.

13) 1.0 ml of dextran-coated charcoal was pipetted into each tube. This was done while the test tube is vortexed so that a homogeneous suspension was attained. Immediately thereafter, the test tube was returned to the crushed ice. The addition of dextran-coated charcoal suspension was limited to 2 minutes. After completing the addition of dextran-coated charcoal, the contents of each tube were mixed again.

14) The test tubes were allowed to incubate at 0° C. in crushed ice for a total of 9 minutes, plus or minus one minute. If pipetting of the dextran-coated charcoal took 2 minutes, then the tube was incubated for 8 minutes past the completion of pipetting.

15) The tubes were immediately centrifuged at 4° C. and 1000×g (2250 rpm) for 10 minutes.

16) The supernatant fluid from each tube was decanted into Aquasol-2 with the same precautions described in step 11) above for the total count tube.

17) The amount of ($^3$H) thromboxane $B_2$ in the supernatant fluid was determined by counting in Beckman LS 7500 spectrophotometer using program 5 for ($^3$H).

Calculation of TX $B_2$ and PG $F_{1alpha}$ Concentrations

The average counts per minute (cpm) for each set of tubes was calculated and the percent $B_0$/TC was derived by using the following equation:

$$\% \; B_0/TC = \frac{(B_0 \text{ cpm} - NSB \text{ cpm})}{(TC \text{ cpm} - \text{background cm})} \times 100$$

A normalized percent bound for each standard and sample was calculated by using the following relationship:

$$\% \; B/B_0 = \frac{(\text{Standard or sample cpm} - NBS \text{ cpm})}{(B_0 \text{ cpm} - NSB \text{ cpm})} \times 100$$

A standard curve was generated by plotting logit % $B/B_0$ as a function of the $\log_{10}$ prostaglandin (TX $B_2$ or PG $F_{1alpha}$) concentration. With this method, the radioimmunoassay data becomes linear and the concentration of TX $B_2$ or PG $F_{1alpha}$ in 100 µl of each sample can be read directly from the standard curve.

Statistical Analysis

One way ANOVA followed by Scheffé multiple range test was employed for treatment comparisons. The accepted level of significance was $p < 0.05$.

RESULTS

ASPIRIN/SALICYLAMIDE PLASMA AND EXCRETION

Effect of Salicylamide on Plasma Total $^{14}$C Following $^{14}$C Aspirin Administration SAM when administered with $^{14}$C-ASA enhanced maximum plasma concentration ($C_{max}$) of total $^{14}$C dose-dependently as shown in FIG. 1. This effect lasted approximately 4 hours following coadministration of the drugs. The concentration of $^{14}$C increase rapidly and reached a plateau then declined in a monoexponential fashion denoting a first-order elimination kinetics with a half-life of 2.8–3.2 hours following the low dose of $^{14}$C-ASA alone or in combination with SAM. The elimination half-life was calculated based on the 6–24 hour plasma concentrations.

Figure 2:
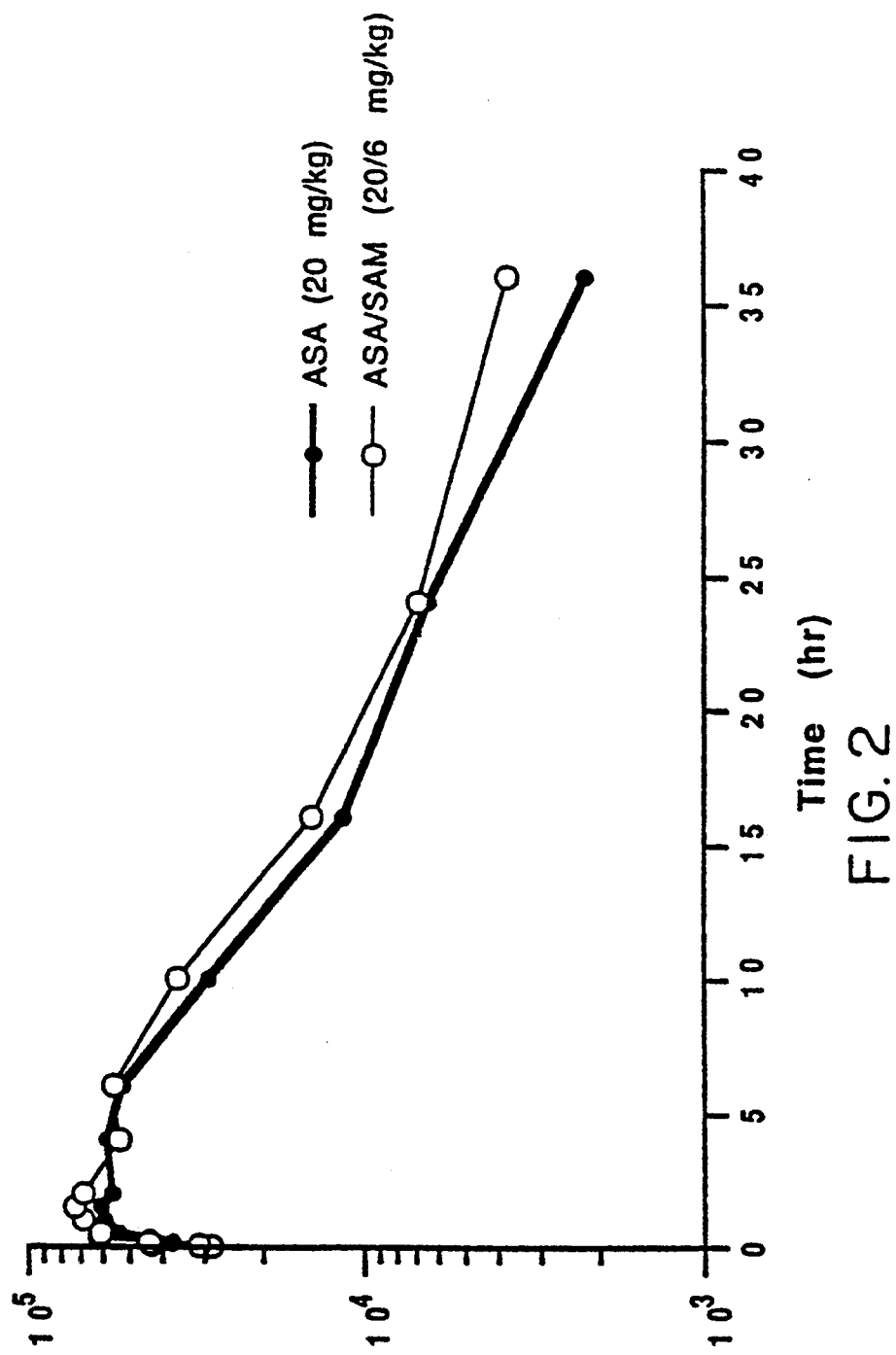
FIG. 2 is a graph of plasma time course of radioactivity following $^{14}$C-aspirin coadministration with salicylamide in high dose. Blood samples were drawn, plasma analysis was conducted, inset description, initials, and data representation are as in FIG. 1.

Following coadministration of $^{14}$C-ASA and SAM in high dose (FIG. 2), $^{14}$C followed a similar pattern in the plasma with an average $T_{\frac{1}{2}\beta}$ of 5.2 hours compared to 5.1 hours following $^{14}$C-ASA administration alone. The data is presented below in Table 1.

TABLE 1

Pharmacokinetic Parameters of $^{14}C$ Following Oral Coadministration of $^{14}C$ Aspirin with Salicylamide

| Parameter[a] | Treatment (mg/kg) | | | | |
|---|---|---|---|---|---|
| | $^{14}C$-ASA (140) | $^{14}C$-ASA/SAM (10/3) | $^{14}C$-ASA/SAM (10/9) | $^{14}C$-ASA (20) | $^{14}C$-ASA/SAM (20/6) |
| $AUC_\infty$ (μg · hr/ml) | 345.7 ± 38.3[b] | 300.7 ± 22.6 | 303.7 ± 16.9 | 810.6 ± 81.7 | 935.1 ± 135.4 |
| $AUC_{4hr}$ (μg · hr/ml) | 99.6 ± 10.6 | 108.8 ± 11.4 | 129.0 ± 9.3 | 222.2 ± 15.3 | 261.9 ± 12.5 |
| $Cl_T$ (ml/hr) | 10.3 ± 1.1 | 11.5 ± 1.0 | 11.1 ± 0.6 | 7.7 ± 0.8 | 7.0 ± 1.1 |
| $T_{\frac{1}{2}\beta}$ (hr) | 3.2 ± 0.2 | 3.1 ± 0.2 | 2.8 ± 0.2 | 5.1 ± 1.2 | 5.2 ± 0.2 |
| $T_{\frac{1}{2}abs.}$ (min) | 9.1 ± 1.1 | 8.7 ± 0.6 | 8.0 ± 0.6 | 8.9 ± 0.9 | 7.4 ± 0.6 |
| $C_{max}$ (μg/ml) | 29.9 ± 2.3 | 34.5 ± 2.7 | 35.6 ± 2.5 | 65.1 ± 8.2 | 82.7 ± 11.2 |
| $V_d$ (ml) | 46.1 ± 2.4 | 46.4 ± 6.4 | 40.6 ± 3.4 | 85.5 ± 28.1 | 97.5 ± 34.1 |

[a]$AUC_\infty$ = area under the plasma concentration vs time curve, $AUC_{4hr}$ = area under the first 4 hr of the plasma concentration vs time curve, $Cl_T$ = total body clearance, $T_{\frac{1}{2}\beta}$ = elimination half-life, $T_{\frac{1}{2}abs}$ = absorption half-life, $C_{max}$ = maximum plasma concentration, $V_d$ = apparent volume of distribution.
[b]Data represents the mean ± standard error, n = 6. SAM coadministration with $^{14}C$-ASA resulted in no significant difference in $^{14}C$ kinetics following either the low or the high dose administration, ANOVA or Student t-test, $p < 0.05$.

SAM enhanced $C_{max}$ of total $^{14}C$ following $^{14}C$-ASA coadministration in the high dose by almost 25%. Following $^{14}C$-ASA administration, the area under the plasma concentration vs. time curve ($AUC_\infty$) of $^{14}C$ showed a dose dependent increase and it was further increased, albeit not significantly, by coadministration of SAM in the high dose. The data revealed that total body clearance ($Cl_T$) of $^{14}C$ following $^{14}C$-ASA was decreased dose-dependently. Concomitant administration of SAM tended to decrease the $Cl_T$ after the high dose combination.

Effect of ASA on Plasma $^{14}C$-SAM Following $^{14}C$-SAM Coadministration

Figure 3:
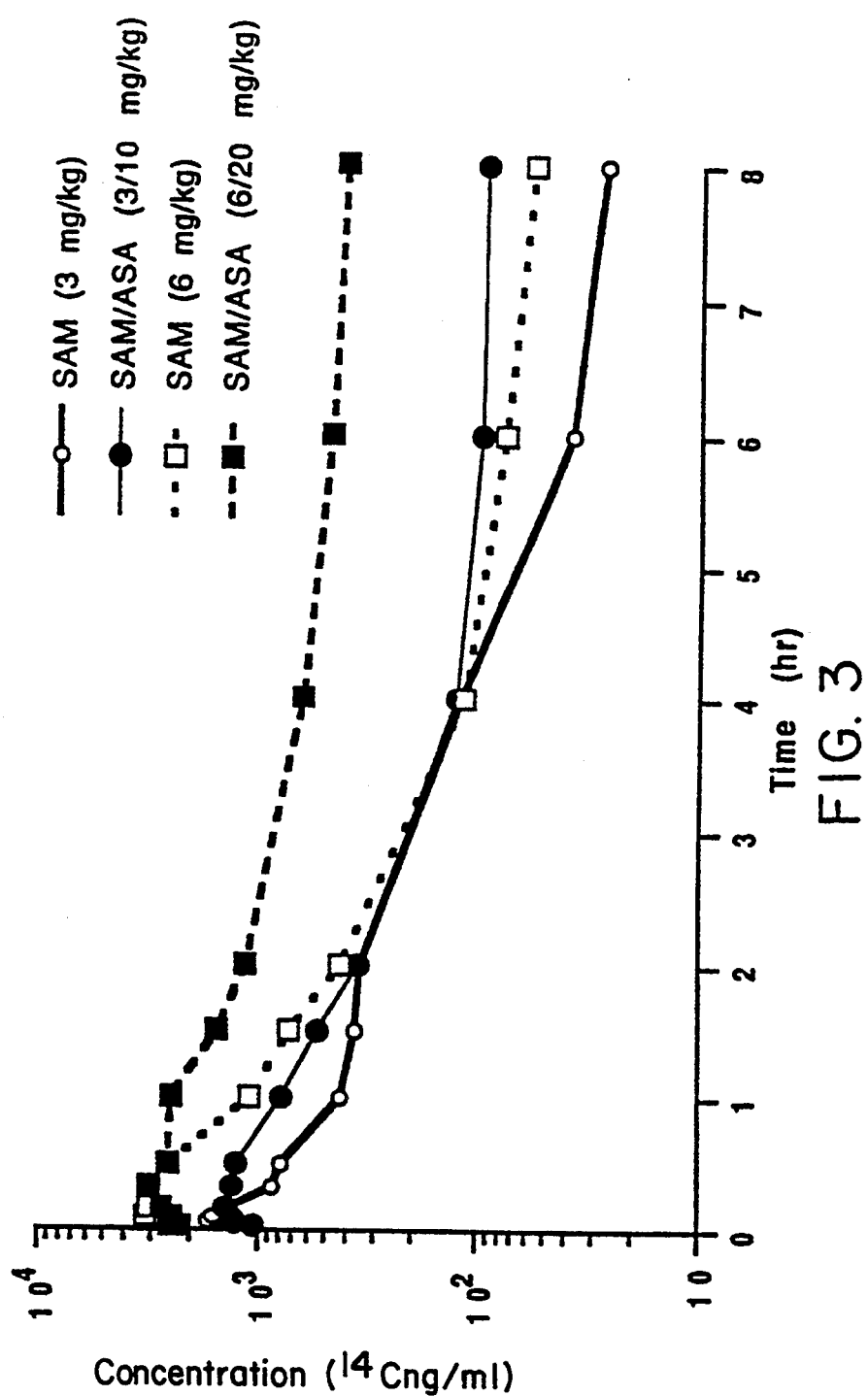
FIG. 3 is a graph of plasma concentration vs. time curve for $^{14}$C following $^{14}$C-salicylamide coadministration with aspirin. Blood samples were taken at the same minute intervals as in Example 1, and at 1, 1.5, 2, 4, 6 and 8 hours. Plasma analysis, abbreviations and data representation are as in FIG. 1.

ASA in low dose (10 mg/kg) did not significantly effect SAM kinetics as shown in Table 2 below (See also, FIG. 3).

TABLE 2

Pharmacokinetic Parameters of $^{14}C$ Following Oral Coadministration of $^{14}C$-Salicylamide with Aspirin

| Parameter[a] | Treatment (mg/kg) | | | |
|---|---|---|---|---|
| | $^{14}C$-SAM (3) | $^{14}C$-SAM/ASA (3/10) | $^{14}C$-SAM (6) | $^{14}C$-SAM/ASA (6/20) |
| $AUC_\infty$ (μ · hr/ml) | 1.9 ± 0.4[b] | 2.6 ± 0.3 | 3.9 ± 0.5 | 8.0 ± 2.2[c] |
| $Cl_{T(ml/hr)}$ | 543.7 ± 89.5 | 401.9 ± 42.8 | 501.1 ± 64.9 | 367.4 ± 116.2 |
| $T_{\frac{1}{2}\beta(hr)}$ | 1.1 ± 0.24 | 1.3 ± 0.08 | 1.1 ± 0.1 | 1.8 ± 0.3[c] |
| $C_{max}$ (μg/ml) | 1.8 ± 0.3 | 1.6 ± 0.3 | 3.7 ± 0.5 | 3.5 ± 0.6 |
| $V_d$ (ml) | 975 ± 152 | 713 ± 34 | 824 ± 156 | 598 ± 171 |

[a]$AUC_\infty$ = area under the plasma concentration vs time curve, $AUC_{4hr}$ = area under the first 4 hr of the plasma concentration vs time curve, $Cl_T$ = total body clearance, $T_{\frac{1}{2}\beta}$ = elimination half-life, $C_{max}$ = maximum plasma concentration, $V_d$ = apparent volume of distribution.
[b]Data represents the mean ± standard error, n = 6.
[c]Significant difference from $^{14}C$-SAM (6), Student t-test, $p < 0.05$.

High dose ASA (20 mg/kg) significantly increased the $AUC_\infty$ and the elimination half-life of $^{14}C$ following $^{14}C$-SAM coadministration in a high dose (6 mg/kg). Aspirin also tended to decrease the total body clearance of SAM following both the low and high dose combinations. The elimination half-life was calculated based on 1-4 hour plasma concentrations.

Overall Excretion of $^{14}C$ Radioactivity Following $^{14}C$-ASA/SAM Coadministration Almost all the $^{14}C$ radioactivity following $^{14}C$-ASA administration alone or in combination with SAM was recovered in urine. The feces contained only 1%-3% of the dose indicating essentially a complete absorption of $^{14}C$-ASA from the gut. No radioactivity was found in the expired air due to either $^{14}C$-ASA or $^{14}C$-$CO_2$. There was no loss of radioactivity during this study evidenced by 100% recovery of the administered dose by the end of the study at 72 hours post-treatment. The results are shown in Table 3 below.

TABLE 3

Overall Excretion of $^{14}C$ Following Oral Coadministration of $^{14}C$ Aspirin with Salicylamide

| | Treatment (mg/kg) | | |
|---|---|---|---|
| | $^{14}C$-ASA (10) | $^{14}C$-ASA/SAM (10/3) | $^{14}C$-ASA/SAM (10/9) |
| Urine | 100.2 ± 0.8[a] | 97.0 ± 1.9 | 98.8 ± 1.0 |
| Faces | 1.0 ± 0.1 | 3.2 ± 1.3 | 1.8 ± 0.5 |
| Total Recovery[b] | 101.7 ± 0.8 | 100.2 ± 1.3 | 100.5 ± 1.1 |

[a]Data represents the mean ± standard error as percentage of the dose, n = 6.
[b]Recovery estimated over 72 hr time-period following treatment administration.

Effect of SAM on the Excretion of Total Radioactivity Following $^{14}C$-ASA Coadministration $^{14}C$ radioactivity was increased in the urine in the 0-8 hour time period following coadministration of SAM with $^{14}C$-ASA. This increase reached significant levels following the 10/9 mg/kg of $^{14}C$-ASA/SAM combination. $^{14}C$ excretion in urine significantly decreased in the period of 8-28 hours following SAM coadministration with $^{14}C$-ASA compared to $^{14}C$-ASA alone (See Table 4 below).

TABLE 4

Urinary Excretion of $^{14}C$ Following Oral Coadministration of $^{14}C$-Aspirin with Salicylamide

| Collection period (hr) | Treatment (mg/kg) | | |
|---|---|---|---|
| | $^{14}C$-ASA (10) | $^{14}C$-ASA/SAM (10/3) | $^{14}C$-ASA/SAM (10/9) |
| 0-8 | 2227 ± 138[a] | 2393 ± 69 | 2573 ± 70[b] |
| 8-16 | 619 ± 124[c] | 508 ± 45 | 318 ± 63 |
| 16-24 | 92 ± 26[d] | 25 ± 5 | 20 ± 4 |
| 24-48 | 60 ± 19[d] | 20 ± 3 | 21 ± 4 |
| 48-72 | 11 ± 3 | 4 ± 0.3 | 7 ± 2 |

TABLE 4-continued

Urinary Excretion of $^{14}$C Following Oral Coadministration of $^{14}$C-Aspirin with Salicylamide

| Collection period (hr) | Treatment (mg/kg) | | |
|---|---|---|---|
| | $^{14}$C-ASA (10) | $^{14}$C-ASA/SAM (10/3) | $^{14}$C-ASA/SAM (10/9) |
| 0–72 | 3055 ± 23 | 3009 ± 39 | 3019 ± 33 |

$^a$Data represents the mean ± standard error in μg $^{14}$C, n = 6.
$^b$Significant difference from $^{14}$C-ASA (10) group, ANOVA, p < 0.05.
$^c$Significant difference from $^{14}$C-ASA/SAM (10/9), ANOVA, p < 0.05.
$^d$Significant difference from $^{14}$C-ASA/SAM (10/3) and 14 C-ASA (10/9), ANOVA, p < 0.05.

Urinary Content of Salicylic Acid, Salicyluric Acid and Salicyl Glucuronides

Figure 4:
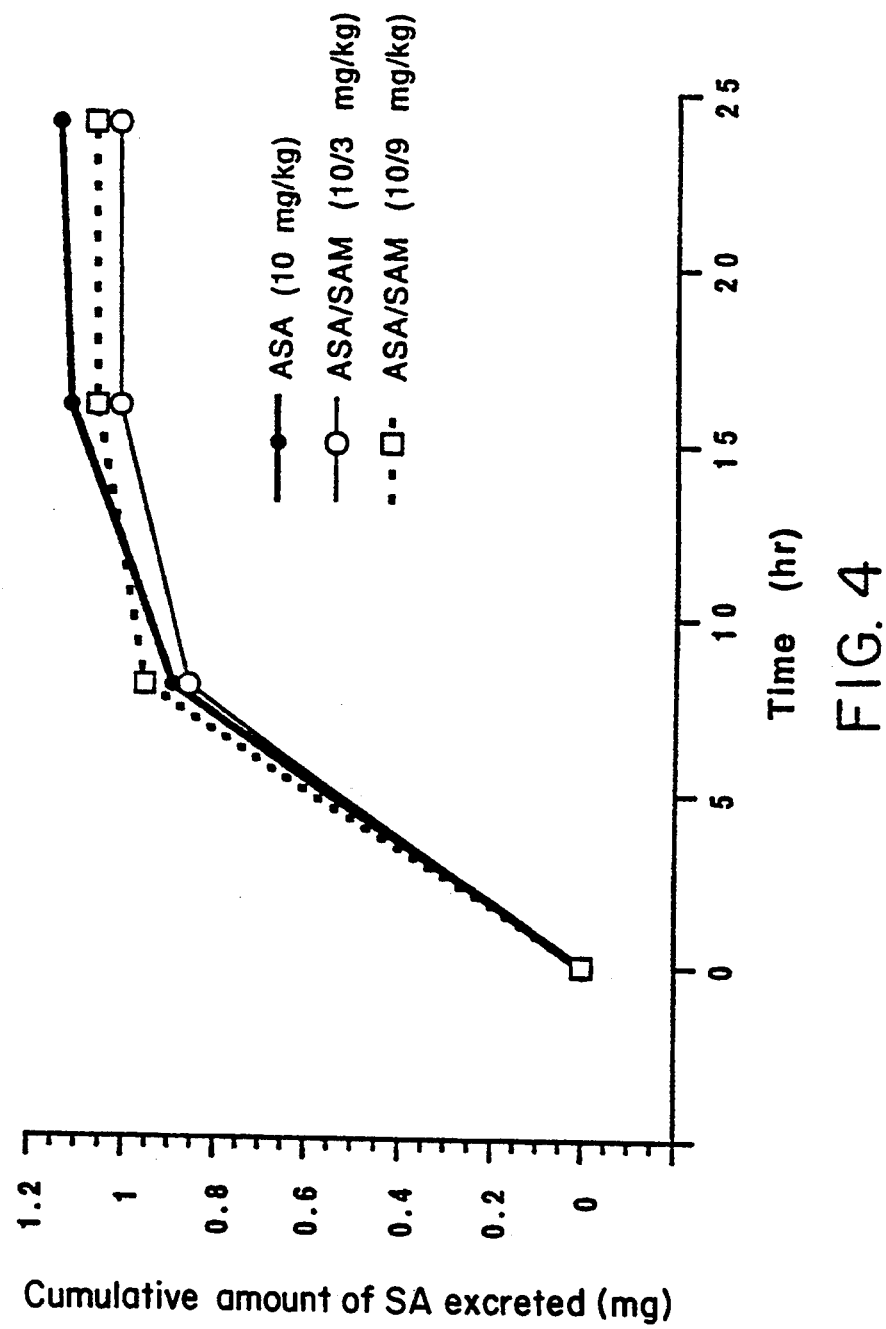
FIG. 4 is a graph of urinary excretion of salicylic acid following ASA/SAM coadministration. Urine was collected at 8, 16 and 24 hours. Analysis was by HPLC for salicylic acid content. Abbreviations and data representation are as in FIG. 1.

SA was the major metabolite found in urine following the administration of $^{14}$C-ASA alone or in combination with low or high dose of SAM. SA accounted for more than 50% of the radioactivity excreted in urine. SA glucuronide accounted for about 35% of the dose excreted in urine while SUA was responsible for approximately 15% of the metabolites in urine. During the period of 0–8 hours following the metabolites in urine, SA, SUA and SA glucuronide were higher in the urine when ASA was coadministered with SAM. Subsequently, however, the urinary content of these metabolites decreased following SAM coadministration compared to $^{14}$C-ASA alone. The excretion of all the metabolites followed a first-order rate pattern evidenced by the hyperbolic curve representing the cumulative amounts excreted in urine vs. time for the first 24 hours following treatment administration. (See FIG. 4 for a plot of excretion of salicylic acid. Other metabolites not shown).

ASPIRIN/SALICYLAMIDE TISSUE DISTRIBUTION STUDIES

Tissue Distribution of $^{14}$C Radioactivity Following $^{14}$C-ASA Administration Table 5 shows the results of the distribution of $^{14}$C Activity following coadministration of $^{14}$C-ASA and SAM in doses of 10/3 mg/kg. A significant increase in total Activity was observed at 1.5 hours post-treatment in plasma, liver, lung, heart, testis, muscle and brain compared to $^{14}$C levels following administration of $^{14}$C-ASA alone. On the other hand, $^{14}$C activity in the stomach (gastric mucosa) was significantly decreased following $^{14}$C-ASA/SAM coadministration in the dose of 10/3 mg/kg, respectively, compared to $^{14}$C-ASA administration in a dose of 10 mg/kg (Table 5). At the 1.5 hour time-point, following ingestion of either $^{14}$C-ASA alone or in combination with SAM, plasma attained the highest concentration of $^{14}$C activity in the body. Following $^{14}$C-ASA administration alone, stomach tissue had the second highest $^{14}$C concentration followed by blood, kidney, skin, liver, lung, upper small intestine, pancreas, heart, testis, red blood cells, muscle, fat, spleen, bone and brain, respectively.

When $^{14}$C-ASA was given to rats in combination with SAM, the plasma attained the highest concentration of $^{14}$C followed by blood, kidney, liver, lung, skin, stomach, heart, testis, upper small intestine, pancreas, spleen, muscle, red blood cells, bone, fat, brain, and washed red blood cells, respectively (See Table 5).

TABLE 5

Tissue Distribution of $^{14}$C Radioactivity in Rats Following Coadministration of $^{14}$C-Aspirin with Salicylamide in Low Dose$^a$

| TISSUE | $^{14}$C-ASA 10 mg/kg | $^{14}$C-ASA/SAM 10/3 mg/kg |
|---|---|---|
| PLASMA | 35.5 ± 1.7$^b$ | 41.2 ± 0.5$^c$ |
| BLOOD | 17.1 ± 3.1 | 19.5 ± 2.2 |
| KIDNEY | 15.1 ± 0.9 | 15.6 ± 0.7 |
| LIVER | 7.9 ± 0.9 | 12.3 ± 0.8$^c$ |
| LUNG | 7.3 ± 0.5 | 11.5 ± 0.6$^c$ |
| SKIN | 8.9 ± 0.4 | 11.3 ± 0.3$^c$ |
| STOMACH | 18.9 ± 3.3 | 10.2 ± 1.2$^c$ |
| HEART | 5.6 ± 0.5 | 7.8 ± 0.3$^c$ |
| TESTIS | 5.1 ± 0.5 | 7.7 ± 0.3$^c$ |
| UPP. SM. INTEST. | 5.8 ± 0.6 | 7.5 ± 0.4 |
| PANCREAS | 5.7 ± 0.4 | 6.3 ± 0.2 |
| SPLEEN | 2.9 ± 0.6 | 4.5 ± 0.2 |
| MUSCLE | 3.5 ± 0.2 | 4.5 ± 0.1$^c$ |
| RBCs | 4.2 ± 1.2 | 4.4 ± 0.5 |
| BONE | 2.7 ± 0.08 | 2.9 ± 0.1 |
| FAT | 3.3 ± 0.1 | 2.7 ± 0.2 |
| BRAIN | 1.5 ± 0.1 | 1.9 ± 0.1$^c$ |
| WASHED RBCs | 1.5 ± 0.5 | 1.4 ± 0.2 |
| BONE MARROW | 0.24 ± 0.05 | 0.29 ± 0.05 |

$^a$ASA = aspirin, SMA = salicylamide, low dose was used.
$^b$Values represent the mean ± st. error of 14C μg/gm tissue (for all except/50 mg of bone marrow) after 1.5 hr of treatment administration, n = 4–6 rats/group.
$^c$Significant difference between $^{14}$C-ASA/SAM and $^{14}$C-ASA alone. P < 0.05, Student t-test.

When $^{14}$C-ASA was administered to rats in a higher dose (20 mg/kg) in combination with SAM (6 mg/kg), a significant increase in distribution of $^{14}$C was noted in the plasma, skin, testis, and brain compared to $^{14}$C-ASA alone (See Table 6).

TABLE 6

Tissue Distribution of $^{14}$C Radioactivity in Rats Following Coadministration of $^{14}$C-Aspirin with Salicylamide in High Dose$^a$

| TISSUE | $^{14}$C-ASA 20 mg/kg | $^{14}$C-ASA/SAM 20/6 mg/kg |
|---|---|---|
| PLASMA | 65.1 ± 1.91 | 84.6 ± 2.1$^c$ |
| BLOOD | 36.1 ± 3.5 | 41.8 ± 4.5 |
| KIDNEY | 32.0 ± 3.2 | 27.6 ± 1.6 |
| SKIN | 21.9 ± 0.6 | 25.2 ± 0.4$^c$ |
| STOMACH | 22.9 ± 4.6 | 21.5 ± 3.4 |
| LIVER | 19.7 ± 0.9 | 20.9 ± 0.7 |
| LUNG | 19.3 ± 0.7 | 19.3 ± 0.9 |
| TESTIS | 14.1 ± 0.6 | 17.6 ± 0.6$^c$ |
| HEART | 17.5 ± 0.5 | 16.8 ± 0.4 |
| UPPER SM. INT. | 15.1 ± 1.0 | 15.4 ± 1.6 |
| PANCREAS | 12.6 ± 0.5 | 11.7 ± 0.4 |
| RBCs | 8.8 ± 1.2 | 10.0 ± 0.8 |
| MUSCLE | 9.5 ± 0.4 | 9.4 ± 0.5 |
| SPLEEN | 10.0 ± 0.9 | 8.8 ± 0.2 |
| BONE | 7.1 ± 0.6 | 8.2 ± 0.3 |
| BRAIN | 4.1 ± 0.07 | 5.3 ± 0.2$^c$ |
| FAT | 4.5 ± 0.3 | 4.5 ± 0.6 |
| WASHED RBCs | 3.8 ± 0.9 | 2.9 ± 0.2 |
| BONE MARROW | 0.79 ± 0.03 | 0.43 ± 0.07$^c$ |

$^a$High dose was administered.
$^b$Values represent the mean ± st. error in $^{14}$C 4 μgm/gm tissue (All except /50 mg bone marrow) after 1.5 hr of treatment administration, n = 4–6 rats/group.
$^c$Significant difference between $^{14}$C-ASA alone and $^{14}$C-ASA/SAM by using Student t-test, p < 0.05.

Contrary to the findings in the low dose combination of $^{14}$C-ASA/SAM, there was no appreciable difference in levels in the lung, heart, muscle, and liver following the high dose combination compared to $^{14}$C-ASA alone. The plasma still had the highest concentration of $^{14}$C in the body followed by the blood and kidney, respectively.

Tissue Distribution of $^{14}C$ Radioactivity following $^{14}C$-SAM Administration Tables 7 and 8 show the distribution of $^{14}C$ radioactivity in various body organs in a descending order of concentration (in $\mu g/gm$ tissue or $\mu g/ml$ plasma). Coadministration of $^{14}C$-SAM with ASA in a dose of 3/10 mg/kg, respectively, enhanced the tissue concentration of $^{14}C$ in the red blood cells, washed red blood cells, bone, fat, skin, testis, muscle and heart compared to when $^{14}C$-SAM was administered alone (See Table 7). After the high dose combination of $^{14}C$ activity was significantly augmented in the liver, lung, red blood cells, and muscle compared to $^{14}C$-SAM administration alone (See Table 8). The data showed that the kidney followed by the stomach were the organs with the highest concentration of $^{14}C$ following administration of $^{14}C$-SAM alone or in combination with ASA in either the low or high dose.

TABLE 7

Tissue Distribution of F $^4C$ Radioactivity in Rats Following Coadministration of $^{14}C$ Salicylamide with Aspirin in Low Dose[a]

| TISSUE | $^{14}C$-SAM 3 mg/kg | $^{14}C$-SAM/ASA 3/10 mg/kg |
|---|---|---|
| KIDNEY | 665 ± 152[b] | 606 ± 101 |
| STOMACH | 550 ± 154 | 275 ± 65 |
| RBCs | 103 ± 9 | 242 ± 39[c] |
| BLOOD | 146 ± 20 | 228 ± 51 |
| WASHED RBCs | 77 ± 10 | 217 ± 53[c] |
| BONE | 60 ± 7 | 191 ± 43[c] |
| FAT | 41 ± 8 | 166 ± 26[c] |
| PLASMA | 147 ± 24 | 153 ± 36 |
| SKIN | 107 ± 10 | 147 ± 8[c] |
| UPP. SM. INTEST. | 130 ± 27 | 144 ± 37 |
| SPLEEN | 83 ± 20 | 142 ± 20 |
| TESUIS | 63 ± 7 | 133 ± 12[c] |
| LIVER | 100 ± 12 | 132 ± 28 |
| PANCREAS | 93 ± 9 | 119 ± 29 |
| LUNG | 91 ± 11 | 107 ± 17 |
| MUSCLE | 56 ± 7 | 100 ± 15[c] |
| HEART | 44 ± 5 | 98 ± 20[c] |
| BRAIN | 27 ± 5 | 36 ± 10 |
| BONE MARROW | 14 ± 2 | 42 ± 13 |

[a]SAM = Salicylamide, ASA = Aspirin, low dose was used.
[b]Values represent the mean ± st. error in $^{14}C$ ngm/gm tissue (for all except /50 mg bone marrow) after 1.5 hr of treatment administration, n = 4–6 rats/groups
[c]Significant difference between $^{14}C$-SAM/ASA and $^{14}C$-SAM alone using Student-t test (p < 0.05).

TABLE 8

Tissue Distribution of $^{14}C$ Radioactivity in Rats Following Coadministration of $^{14}C$-Salicylamide with Aspirin in High Dose[a]

| TISSUE | $^{14}C$-SAM 6 mg/kg | $^{14}C$-SAM/ASA 6/20 mg/kg |
|---|---|---|
| KIDNEY | 1358 ± 441[b] | 1354 ± 251 |
| STOMACH | 832 ± 217 | 439 ± 106 |
| SKIN | 240 ± 11 | 331 ± 45 |
| LIVER | 136 ± 12 | 310 ± 61[c] |
| UPP. SM. INTEST. | 268 ± 34 | 310 ± 21 |
| LUNG | 218 ± 12 | 291 ± 16[c] |
| PLASMA | 237 ± 49 | 243 ± 73 |
| BLOOD | 198 ± 32 | 243 ± 25 |
| SPLEEN | 200 ± 26 | 221 ± 24 |
| RBCs | 118 ± 22 | 196 ± 4[c] |
| BONE | 153 ± 38 | 179 ± 40 |
| FAT | 130 ± 14 | 179 ± 32 |
| TESTIS | 155 ± 17 | 175 ± 43 |
| PANCREAS | 147 ± 9 | 163 ± 39 |
| WASHED RBCs | 92 ± 12 | 129 ± 21 |
| HEART | 106 ± 10 | 120 ± 13 |
| MUSCLE | 78 ± 3 | 103 ± 2[c] |
| BRAIN | 33 ± 1 | 42 ± 5 |
| BONE MARROW | 29 ± 17 | 12 ± 1 |

[a]High dose was administered.
[b]Values represent the mean ± st. error in $^{14}C$ ngm/gm tissue (or ngm/50 mg bone marrow) for n = 4–6 rats/group
[c]Significant difference between $^{14}C$-SAM/ASA and $^{14}C$-SAM alone using student-t test (P < 0.05).

Tissue Distribution of Salicylic Acid (SA)

Table 9 illustrates the distribution of $^{14}C$-SA following the administration of $^{14}C$-ASA alone or in combination with SAM. At 1.5 hours following coadministration of $^{14}C$-ASA and SAM at a dose of 10/3 mg/kg, the tissue levels of $^{14}C$-SA were significantly enhanced in the liver, lung, heart, and plasma when compared to tissue levels following administration of $^{14}C$-ASA alone.

Following the administration of $^{14}C$-ASA/SAM (20/6 mg/kg), $^{14}C$-SA levels in the lung, heart, and plasma were significantly increased compared to when $^{14}C$-ASA was administered alone.

Kidney levels of $^{14}C$-SA were not markedly altered by coadministration of SAM with $^{14}C$-ASA at both low and high doses. The same was true for $^{14}C$-SA levels in the liver following the high dose combination of $^{14}C$-ASA/SAM (20/6 mg/kg) ( See Table 9).

TABLE 9

Tissue Distribution of $^{14}C$- Salicylic Acid (SA) Following Oral Coadministration of $^{14}C$-Aspirin with Salicylamide[a]

| | Treatment (mg/kg) | | | |
|---|---|---|---|---|
| Tissue | $^{14}C$-ASA (10) | $^{14}C$-ASA/SAM (10/3) | $^{14}C$-ASA (20) | $^{14}C$-ASA/SAM (20/6) |
| LIVER | 3.74 ± 0.54[b] | 5.16 ± 0.25[c] | 9.59 ± 0.14 | 10.11 ± 0.64 |
| KIDNEY | 5.26 ± 0.58 | 6.16 ± 0.44 | 13.17 ± 0.92 | 12.02 ± 0.65 |
| LUNG | 4.33 ± 0.42 | 5.60 ± 0.29[c] | 8.10 ± 0.31 | 9.76 ± 0.39[d] |
| HEART | 2.51 ± 0.29 | 3.46 ± 0.22[c] | 6.88 ± 0.24 | 7.73 ± 0.25[d] |
| PLASMA | 15.55 ± 0.66 | 20.24 ± 0.66[c] | 30.91 ± 2.88 | 41.29 ± 3.74[d] |

[a]Distribution was studied 1.5 hr following oral administration of the treatments.
[b]Data represent the mean standard error in $\mu g/gm$ tissue or ml plasma, n = 6.
[c,d]Significant difference from ASA (10) and ASA (20) groups, respectively, Student t-test, p < 0.05.

Tissue Distribution of ASA, GA, DBA, and SUA

Salicyluric acid was evaluated as a function of the coadministration of aspirin and salicylamide. The results are summarized below in Table 10. The parent compound, aspirin, was not detected in any of the tissues studied, i.e., plasma, lung, liver, heart and kidney at 1.5 hours after the administration of $^{14}C$-ASA alone or in combination with SAM at both the low and high doses.

$^{14}$C-Salicyluric acid (SUA), one of the major metabolites of SA, was detected in the kidney following the administration of $^{14}$C-ASA alone and in combination with SAM and at both the low and high doses. However, no significant difference was found between $^{14}$C-SUA kidney levels following the administration of $^{14}$C-ASA with or without SAM at either the low or high doses (See Table 10 below). SUA was not detected in the other tissues studied, i.e., lung, heart, liver, and plasma. With regard to gentisic acid (GA) and 2,3-dihydroxybenzoic acid (DBA), the minor metabolites of ASA, both metabolites were not detected in any of the aforementioned tissues that were studied and at either the low or high dose administered.

Using acid hydrolysis of tissue samples followed by HPLC characterization and quantitation of $^{14}$C-SA, the acid-hydrolyzed fraction of $^{14}$C-SA in tissues was found to be significantly higher in kidney only following $^{14}$C-ASA/SAM (10/3 mg/kg) coadministration and in the plasma only following the high dose combination (See Table 12 below). SAM coadministration with $^{14}$C-ASA did not affect the tissue concentration of the acid-hydrolyzed fraction of $^{14}$C-SA in the liver at either the low or the high dose combinations. The acid-hydrolyzed fraction of SA is comprised of SA glucuronides and some of the protein-bound SA.

TABLE 12

Tissue Distribution of Acid-Hydrolysed $^{14}$C-Salicylic Acid Fraction Following Oral Coadministration of $^{14}$C-Aspirin with Salicylamide[a]

| Tissue | Treatment (mg/kg) | | | |
|---|---|---|---|---|
| | $^{14}$C ASA (10) | $^{14}$C-ASA/SAM (10/3) | $^{14}$C-ASA (20) | $^{14}$C-ASA/SA (20/6) |
| LIVER | 0.00 ± 0.00[a] | 1.02 ± 0.62 | 13.71 ± 6.15 | 8.43 ± 5.25 |
| KIDNEY | 13.84 ± 2.57 | 3.94 ± 1.44[c] | 11.91 ± 5.16 | 0.37 ± 0.37 |
| PLASMA | 16.72 ± 6.65 | 21.83 ± 12.90 | 4.88 ± 3.06 | 43.69 ± 11.91[d] |

[a]Distribution was studied 1.5 hr following oral administration of the treatments.
[b]Data represent the mean standard error in μg/gm tissue or ml plasma, n = 6 rats/group.
[c,d]Significant difference from $^{14}$C-ASA (10) and $^{14}$C-ASA (20) groups, respectively, Student t-test, $p < 0.05$.

Tissue Distribution of SAM and GAM

The parent compound SAM was not detected in

TABLE 10

Tissue Distribution of $^{14}$C-Salicyluric Acid Following Oral Coadministration of $^{14}$C-Asipirin (ASA) with Salicylamide (SAM)hu a

| Tissue | Treatment (mg/kg) | | | |
|---|---|---|---|---|
| | $^{14}$C-ASA (10) | $^{14}$C-ASA/SAM (10/3) | $^{14}$C-ASA (20) | $^{14}$C-ASA/SAM (20/6) |
| LIVER | ND[b] | ND | ND | ND |
| KIDNEY | 0.61 ± 0.16[c] | 1.05 ± 0.21 | 0.44 ± 0.27 | 0.72 ± 0.32 |
| PLASMA | ND | ND | ND | ND |

[a]Distribution was studied 1.5 hr following oral administration of the treatments.
[b]ND = not detected
[c]Data represent the mean ± standard error in μg/gm tissue or ml plasma, n = 6 rats/group.

Tissue Tightly Protein-Bound $^{14}$C Activity Following $^{14}$C-ASA Administration The tissue tightly protein-bound $^{14}$C radioactivity was significantly higher in liver, lung, and heart following $^{14}$C-ASA/SAM (10/3 mg/kg) coadministration compared to when $^{14}$C-ASA was given alone (See Table 11). However, this effect did not reach significant levels when $^{14}$C-ASA was coadministered with SAM at higher dose (20/6 mg/kg, respectively). Kidney concentration of tightly protein-bound $^{14}$C was not influenced by concomitant administration of SAM with $^{14}$C-ASA at both low and the high doses.

plasma 1.5 hours following the administration of both $^{14}$C-SAM alone and in combination with ASA at low and high doses. Following coadministration of ASA with $^{14}$C-SAM, $^{14}$C-SAM levels were significantly lower in lung at both the low and high dose combinations compared to $^{14}$C-SAM administration alone. When $^{14}$C-SAM concentration in the kidney was studied following its coadministration with ASA, it was found to be significantly reduced following the low dose combination. Following $^{14}$C-SAM/ASA (6/20 mg/kg), $^{14}$C-SAM was also decreased in the kidney by about 30% compared to $^{14}$C-SAM alone.

TABLE 11

Tissue Tightly Protein-Bound $^{14}$C Radioactivity Following Oral Coadministration of $^{14}$C-Asipirin with Salicylamide[a]

| Tissue | Treatment (mg/kg) | | | |
|---|---|---|---|---|
| | $^{14}$C-ASA (10) | $^{14}$C-ASA/SAM (10/3) | $^{14}$C ASA (20) | $^{14}$C-ASA/SAM (20/6) |
| LIVER | 3.93 ± 0.04[c] | 4.63 ± 0.26[c] | 9.81 ± 0.12 | 9.91 ± 0.59 |
| KIDNEY | 3.85 ± 0.30 | 4.01 ± 0.17 | 11.66 ± 0.29 | 13.00 ± 1.00 |
| LUNG | 1.62 ± 0.14 | 3.83 ± 0.19[c] | 5.84 ± 0.40 | 6.45 ± 0.26 |
| HEART | 2.30 ± 0.28 | 3.86 ± 0.10[c] | 5.79 ± 0.40 | 6.31 ± 0.21 |
| PLASMA | 26.95 ± 2.67 | 127.84 ± 1.48 | 41.32 = 1.74 | 45.61 ± 4.05 |

[a]Distribution of $^{14}$C was studied 1.5 hr following oral administration of the treatments.
[b]Data represent the mean ± standard error in μg $^{14}$C/gm tissue or ml plasma, n = 4–6.
[c]Significant difference from ASA (10) group, Student t-test, $p < 0.05$.

The Acid-Hydrolyzed Fraction of SA in Liver, Kidney and Plasma $^{14}$C-SAM level in the liver was about 50% higher when $^{14}$C-SAM was coadministered with ASA at the lower dose combination. This effect was noticed when the high dose combination was administered (See Table 13 below). $^{14}$C-SAM was not detected in the heart after $^{14}$-SAM (3 mg/kg) administration with or without ASA (10 mg/kg). After $^{14}$C-SAM alone (6 mg/kg), $_{14}$C-SAM was detected in the heart while it was under the study detection limits when measured at 1.5 hours following administration of $^{14}$C-SAM/ASA (6/20 mg/kg) dose.

or 120 μg/ml, respectively) was coadministered with ASA, it did not influence ASA inhibition of TX B$_2$ synthesis. When SAM was administered 10 minutes before the addition of ASA (SAM→ASA), there was still no blocking effect of SAM on ASA-induced inhibition of cyclooxygenase.

Interaction of Salicylamide and Salicylic Acid on Platelet TX B$_2$ Synthesis

TABLE 13

Tissue Distribution of $^{14}$C-Salicylamide Following oral Coadministration of $^{14}$C-Salicylamide with Aspirin[a]

| Tissue | Treatment (mg/kg) | | | |
|---|---|---|---|---|
| | $^{14}$C-SAM (3) | $^{14}$C-SAM/ASA (3/10) | $^{14}$C-SAM (6) | $^{14}$C-SAM/ASA (6/20) |
| LIVER | 16.6 ± 5.3[b] | 23.0 ± 3.2 | 29.4 ± 3.3 | 31.3 ± 4.0 |
| KIDNEY | 152.1 ± 13.4 | 80.9 ± 11.5[c] | 181.4 ± 18.3 | 129.9 ± 23.8 |
| LUNG | 17.1 ± 3.0 | 2.2 ± 1.5[c] | 41.9 ± 3.9 | 16.2 ± 4.2[d] |
| HEART | ND[e] | ND | 2.9 ± 1.7 | ND |
| PLASMA | ND | ND | ND | ND |

[a]Distribution of $^{14}$C-SAM was studied 1.5 hr following oral administration of the treatments.
[b]Data represent the mean ± standard error in ng/gm tissue or ml plasma, n = 6.
[c,d]Significant difference from $^{14}$C-SAM (3) and $^{14}$C-SAM (6) groups, respectively, Student t-test, p < 0.05.
[e]Not detected.

Tissue Tightly Protein-Bound $^{14}$C Radioactivity Following $^{14}$C-SAM Administration The data showed that tissue tightly protein-bound $^{14}$C radioactivity was significantly increased in the liver following coadministration of $^{14}$C-SAM and ASA at both the low and the high doses (See Table 14 below). In the plasma as well as the kidney, the tissue tightly protein-bound $^{14}$C radioactivity was not altered by coadministration of the combination in either the low or high doses. Tissue tightly protein-bound $^{14}$C radioactivity tended to be higher in the lung after coadministration of $^{14}$C-SAM with ASA in the low dose. This effect reached a significant level after the high dose combination compared to when $^{14}$C-SAM was given alone. In the heart, coadministration of ASA with $^{14}$C-SAM significantly enhanced tissue tightly protein-bound $^{14}$C radioactivity after the low dose combination. This effect was not noticed following the high dose combination of $^{14}$C-SAM/ASA (6/20 mg/kg).

Figure 6:
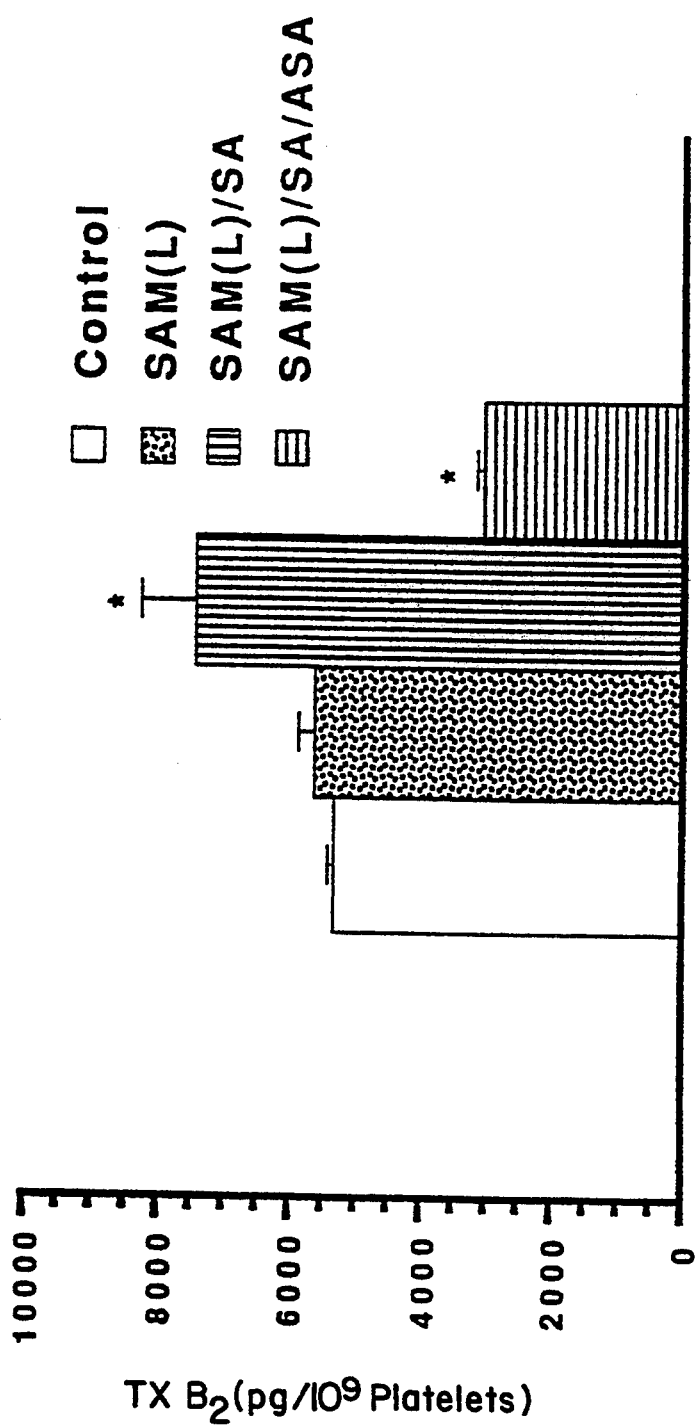
FIG. 6 is a bar graph of the effects of salicylamide and salicylic acid on thromboxane $B_2$ and modification of the effects upon administration of aspirin. TX $B_2$ production from platelet-rich plasma was studied after treatment followed in 10 minutes by arachidonic acid stimulation. TX $B_2$=thromboxane $B_2$, SAM(L)=salicylamide in low dose (40 mcg/ml), SA=salicylic acid (130 mcg/ml), ASA=aspirin (130 mcg/ml). * indicates a significant difference from control, $p<0.05$, ANOVA. The columns represent the mean values+- SEM, n=3-5.

Coadministration of SAM and SA in a ratio of 10:3 (w/w) resulted in a significant increase in TX B$_2$ production compared to the control. Addition of ASA to the treatment combination resulted in a significant blocking of platelet cyclooxygenase evidenced by diminished TX B$_2$ formation (See FIG. 6).

Figure 7:
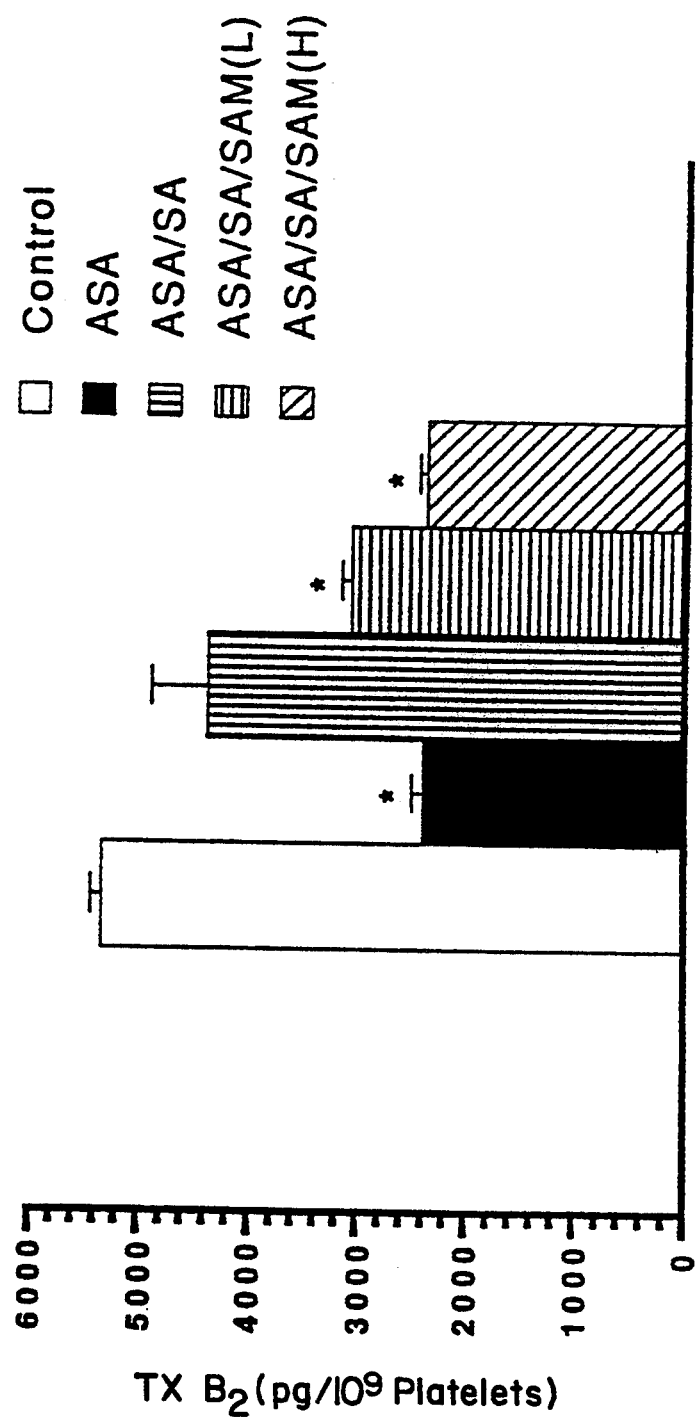
FIG. 7 is a bar graph of the reversal of the antagonistic effects of salicylic acid on aspirin induced inhibition of thromboxane $B_2$ synthesis by salicylamide. TX $B_2$ studied as in FIGS. 5 and 6. SAM(L) as defined in FIG. 6. SAM(H) as defined in FIG. 5. * and column values as defined in FIG. 6.

Salicylamide Reversal of the Aspirin-Antagonistic Effect of Salicylic Acid on Platelet Cyclooxygenase When the platelets were treated with ASA/SA (1:1, w/w) concomitantly, a significant blocking of ASA inhibitory effect on TX B$_2$ synthesis was observed (See FIG. 7). SA in this concentration ratio was able to antagonize ~70% of ASA effect and TX B$_2$ levels were not different from the control. When SAM was coadministered with ASA/SA treatment it reversed the effect of SA by ~60% when applied in the low dose (40 μg/ml) and completely preempted SA effect when applied in the high dose (120 μg/ml).

Salicylamide Potentiation of Aspirin Effect on Vascular

TABLE 14

Tissue Tightly Protein-Bound $^{14}$C Radioactivity Following Oral Coadministration of $^{14}$C-Salicylamide with Aspirin[a]

| Tissue | Treatment (mg/kg) | | | |
|---|---|---|---|---|
| | $^{14}$C-SAM (3) | $^{14}$C-SAM/ASA (3/10) | $^{14}$C-SAM (6) | $^{14}$C-SAM/ASA (6/20) |
| LIVER | 24.2 ± 4.0[b] | 35.5 ± 2.7[c] | 72.6 ± 10.7 | 170.9 ± 22.3[d] |
| KIDNEY | 669.0 ± 45.1 | 459.7 ± 108.0 | 1104.5 ± 212.6 | 1030.0 ± 216.0 |
| LUNG | 43.1 ± 6.1 | 56.8 ± 4.7 | 134.8 ± 20.7 | 217.9 ± 15.8[d] |
| HEART | 20.6 ± 1.7 | 38.2 ± 3.3[c] | 87.7 ± 11.0 | 90.7 ± 5.0 |
| PLASMA | 57.8 ± 3.0 | 60.1 ± 3.5 | 154.6 ± 29.8 | 173.8 ± 49.0 |

[a]Distribution of $^{14}$C was studied 1.5 hr following oral administration of the treatments.
[b]Data represent the mean ± standard error in ng $^{14}$C/gm tissue or ml plasma, n = 6.
[c,d]Significant difference from $^{14}$C-SAM (3) and $^{14}$C-SAM (6) group, respectively, Student t-test, p < 0.05.

ASPIRIN/SALICYLAMIDE FUNCTIONAL STUDIES

Effect of Salicylamide and/or Aspirin on Platelet Cyclooxygenase

Figure 5:
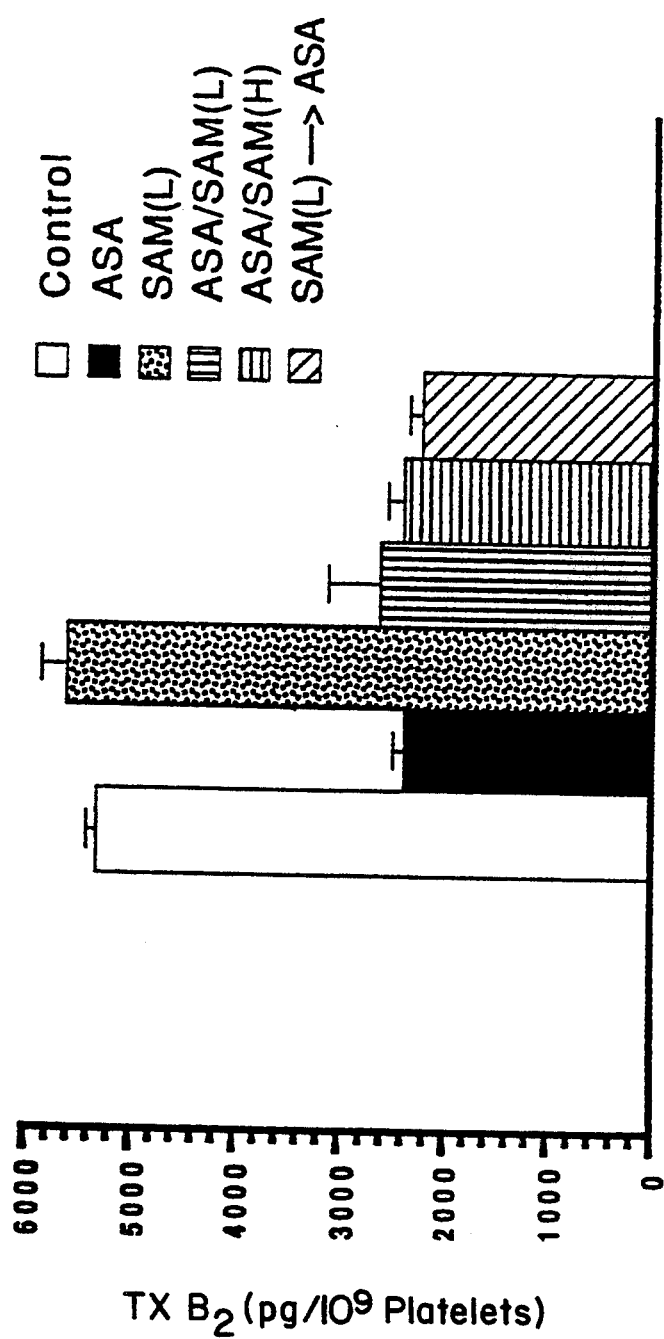
FIG. 5 is a bar graph of the effects of aspirin and salicylamide on thromboxane $B_2$ (TX $B_2$) production by platelet rich plasma. TX $B_2$ production from platelet-rich plasma was studied after treatment followed 10 minutes by arachidonic acid stimulation. TX $B_2$=thromboxane $B_2$, ASA and SAM are as described above in FIG. 1, (L)=low dose (40 mcg/ml), (H)=high dose (120 mcg/ml), SAM(L)→ASA=SAM administration followed 10 min later by ASA administration. * indicates a significant difference from control and SAM(L). $p<0.05$, ANOVA. The columns represent the mean+SEM. n=5.

ASA showed an inhibition of platelet cyclooxygenase as evidenced by significant inhibition of TX B$_2$ formation (See FIG. 5). SAM alone did not change TX B$_2$ production compared to control (AA-stimulated PRP). When SAM at either the low (L) or high (H) dose (40

Cyclooxygenase ex vivo

Figure 8:
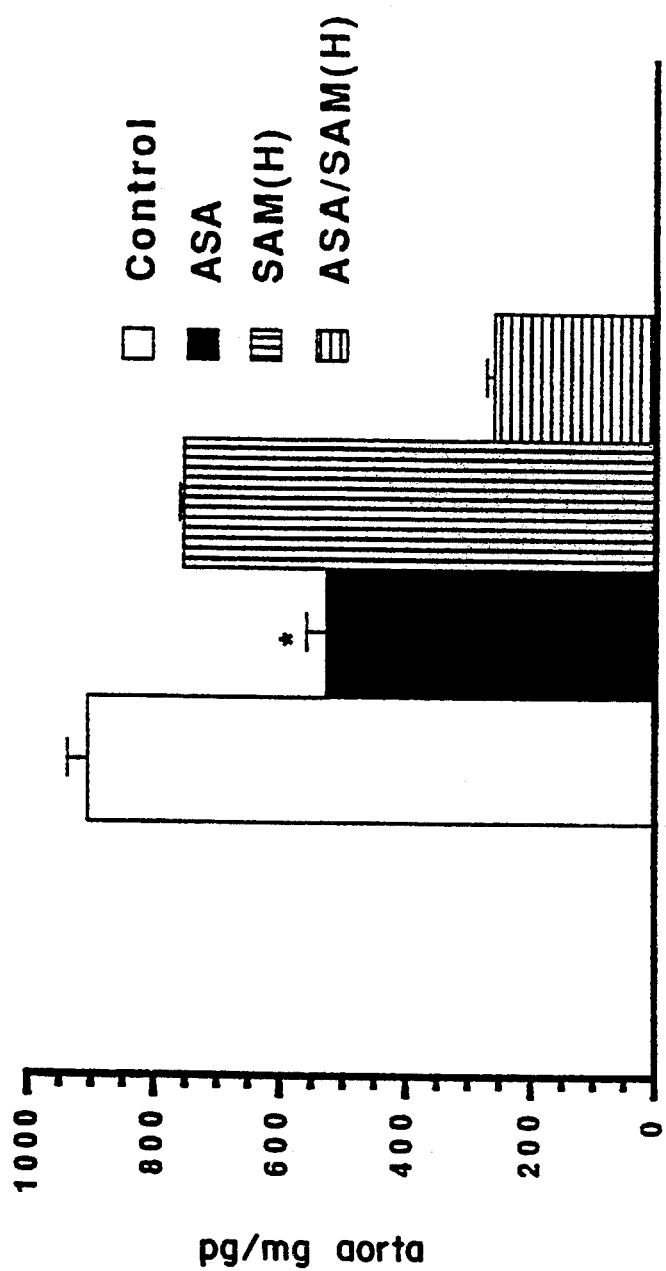
FIG. 8 is a bar graph of the effect of aspirin and/or salicylamide on 6-keto PG $F_{1\alpha}$ synthesis by rat thoracic aortic tissue ex vivo. ASA=aspirin (10 mg/kg). SAM(H)=salicylamide in high dose (9 mg/kg). * indicates a significant difference from control and ASA/SAM(H). ** indicates a significant difference from control, ASA, and SAM(H). The columns represent the mean values+SEM, n=3-4, $p<0.05$. ANOVA.

ASA alone, in a dose of 10 mg/kg, inhibited PG I$_2$ measured as its stable metabolite 6-keto PG F$_{1alpha}$ from rat thoracic aortic rings. SAM alone could partially, but still significantly, block vascular cyclooxygenase activity when administered in a dose of 9 mg/kg to rats. Coadministration of SAM and ASA resulted in a pronounced potentiation of the inhibitory effect of ASA on vascular cyclooxygenase evidenced by a drop of the level of 6-keto PG F$_{1alpha}$ to only 28% of the control (See FIG. 8).

The interaction of ASA and SAM upon oral coadministration to rats with regard to plasma and excretion kinetics indicated that SAM, when coadministered with $^{14}$C-ASA, dose-dependently increases the plasma level of total $^{14}$C radioactivity. The increased plasma level of $^{14}$C following coadministration of $^{14}$C-ASA and SAM was followed by a rapid decline of plasma levels of radioactivity most likely due to enhanced excretion proportional to and associated with the higher plasma levels achieved.

The bioavailability of $^{14}$C was found to be 100% in the excretion study. This may explain the equal AUC$_\infty$ obtained for $^{14}$C-ASA alone and in combination with SAM in both the low and high doses employed. One explanation for the higher $^{14}$C levels found in 8-hour urine following $^{14}$C-ASA/SAM coadministration is competition of SAM and SA for plasma protein binding, resulting in displacement of SA from its binding sites, and enhancing its excretion. The distribution studies (vide infra) in rats showed that SAM coadministration with $^{14}$C-ASA significantly increased the free fraction of $^{14}$C-SA in the plasma. A combination of both mechanisms, i.e., competition for glucuronidation and plasma protein binding, appears to be a plausible explanation for the results obtained.

The excretion study of low dose ASA demonstrated that the elimination of SA, SUA and salicyl glucuronide proceeded in a first-order rate fashion. Similar results have been obtained in rats for comparable doses of ASA. The coadministration of SAM with $^{14}$C-ASA in the low doses employed did not affect the pattern of excretion of ASA metabolites in urine.

ASA in high doses increased the elimination half-life and AUC$_\infty$ of $^{14}$-SAM activity, which may be a result of a competition between SA and SAM glucuronides for the organic acid secretion pathway in the renal tubules. SA has also been proven to noncompetitively inhibit sulfation of SAM and hence can decrease its clearance and account for the observed increase in its half-life. The increase in $c_{max}$ of $^{14}$C following $^{14}$C-ASA/SAM coadministration would be expected to increase the efficacy of the combination especially following the high dose combination.

There was no effect of SAM on $^{14}$C-ASA absorption half-life excluding any interaction between ASA and SAM during the absorption process which proceeds in a first-order rate. This is evidence that the observed interaction between ASA and SAM most probably occurs during their biotransformation and/or protein binding.

The 1.5 hour time-point was chosen to study the distribution of ASA, SAM, and their metabolites based on a preliminary study that had shown $^{14}$C radioactivity to plateau at that time following $^{14}$C-ASA administration. Also, 1.5 hours following $^{14}$C radioactivity in the plasma started to decline indicating that a state of dynamic equilibrium had been obtained which is best for studying the distribution of compounds. Moreover, the 1.5 hour time-point would allow testing for the presence of ASA, the parent compound in tissues.

The data showed that ASA itself was not detected in the plasma after 1.5 hours of its administration alone or with SAM. ASA was hydrolyzed so rapidly that by 1.5 hours following its administration, its metabolites, especially SA, were responsible for all the $^{14}$C radioactivity detected in tissues.

Following coadministration of SAM with $^{14}$C-ASA, a discernable and parallel increase in $^{14}$C radioactivity and $^{14}$C-SA was observed in plasma, liver and lung. A similar increase in $^{14}$C-SA would be expected in skin, testis, muscle, and brain in which $^{14}$C radioactivity was significantly increased. The higher plasma $^{14}$C concentrations could be attributed to a competition of ASA and/or SA with SAM for the glucuronidation pathway. A second explanation would be a competition between SA and SAM for plasma protein binding which renders more free SA available for tissue distribution.

The gastric mucosa had a lower concentration of $^{14}$C radioactivity following coadministration of $^{14}$C-ASA with SAM in low doses. This effect may be due to a competition among ASA and/or SA with SAM for gastric mucosal receptors.

An important observation is the parallel relationship of total $^{14}$C radioactivity and $^{14}$C-SA concentrations in tissues. Most of the $^{14}$C radioactivity in tissues following administration of $^{14}$C(carboxyl)-ASA or $^{14}$C(carboxyl)-ASA/SAM is believed to be attributed to $^{14}$C(carboxyl)-SA. However, the presence of SA glucuronides in the liver and kidney and SUA in the kidney should be taken into account.

There was a significant increase in the $^{14}$C-ASA-related radioactivity in the skin, muscle, and brain which are presumably important sites of analgesic action of ASA and SA.

Changes in tissue perfusion, intrinsic tissue clearance, plasma protein binding, and tissue receptor binding are all factors that may play a role in any drug-drug interaction. When two doses, low and high, of the coadministered compounds are employed, the interaction becomes even more complicated especially when taking into consideration the pharmacokinetics of SAM and salicylic acid which are dose-dependent.

The lack of a parallel increase in the tissue levels of $^{14}$C radioactivity following coadministration of $^{14}$C-ASA with SAM in some tissues despite significantly higher plasma levels may be explained by a local interaction on the tissue level, e.g., effect on tissue perfusion, or by a difference in the time to equilibrium between $^{14}$C in plasma and in some tissues.

It is also important to note that ASA, SA and SAM are vasoactive drugs that can affect the prostaglandin levels, which in turn are major determinants of local tissue perfusion.

$^{14}$C-Salicyluric acid was detected in the kidney following administration of $^{14}$C-ASA alone or in combinations with SAM. This suggests that the kidney plays an important role in glycine conjugation of salicylic acid. The liver had no detectable level of SUA.

The data presented with regard to $^{14}$C radioactivity in tissues following coadministration of $^{14}$C-SAM with ASA in low doses demonstrates a significant elevation in RBCs, bone, fat, skin, muscle, and heart when compared to administration of $^{14}$C-SAM alone. The high dose combination of $^{14}$C-SAM/ASA resulted in a significantly higher concentration of $^{14}$C radioactivity in the liver, lung, RBCs and heart compared to the control ($^{14}$C-SAM alone). In both cases, the increase in $^{14}$C radioactivity in tissues was not accompanied by an increase in the plasma levels of radioactivity, and hence may be attributed to a local effect of ASA on tissue perfusion which would lead to a decrease in tissue clearance of SAM and an enhancement in $^{14}$C tissue concentrations.

Another mechanism by which ASA or SA might influence tissue concentrations of SAM and/or its metabolites is by direct competition with SAM for the glucuronidation pathway, thereby altering the ratio between SAM and SAM glucuronide in the tissue. SA can decrease its clearance and increase its tissue concentration. The observed decrease in $^{14}$C-SAM distribution in kidney following coadministration of $^{14}$C-SAM-/ASA is consistent with a decrease in SAM clearance since SAM is excreted mainly through the kidney.

The higher plasma levels achieved by SA during this study may amplify the interaction of SA and ASA on platelet and vascular cyclooxygenase. The higher SA levels can increase the therapeutic efficacy of the combination of ASA/SAM, since SA may exert its analgesic and anti-inflammatory effects by mechanisms other than inhibiting cyclooxygenase.

Interaction of Aspirin and Salicylamide on Platelet and Vascular Cyclooxygenase

SAM fulfills the minimal structural criteria necessary to occupy the putative supplementary site on cyclooxygenase, i.e., a phenol structure.

SAM did not alter ASA-induced inhibition of platelet cyclooxygenase even when applied before ASA while it was able to dose-dependently quench the aspirin-antagonistic effect of SA.

The observed enhancement of TX $B_2$ production from platelets upon treatment with SAM/SA combination could be explained by the inhibitory effect of SA on lipooxygenase, which may lead to shunting of arachidonic acid (AA) cascade to the cyclooxygenase pathway.

The ex vivo data presented indicate that there is a significant potentiation of SAM to the anticyclooxygenase effect of ASA. This can be explained, in view of the evidence presented in this study, by SAM competition with SA for the mutual cyclooxygenase receptor and, hence, allowing ASA to act unopposed on the enzyme with consequent enhanced efficacy in abrogating PG $I_2$ production from the rat thoracic aorta. Since SAM itself has no effect in vitro on cyclooxygenase, the reported ex vivo effect of SAM on the aortic cyclooxygenase may be due to an inhibitory effect by one of its metabolites, most likely gentisamide.

The therapeutic Effects of ASA/SAM Combinations

The reversal by SAM of SA antagonism of ASA-induced cyclooxygenase inhibition as well as the enhancement of plasma levels of SA could have a significant therapeutic impact for ASA/SAM combinations.

With regard to the antithrombotic effect of ASA, the combination of SAM and ASA offers advantages toward achieving the long-sought differential effect of ASA on platelet and vascular cyclooxygenase. Without limiting the invention to a particular mechanism of action, SAM may protect ASA, especially in the presystemic circulation, from any SA inactivation. Likewise, SAM may allow a reduction of the dose of ASA administered to achieve the same antithrombotic effect, resulting in fewer adverse effects, a very desirable outcome specially for prolonged ASA treatment. The higher SA plasma levels achieved by ASA/SAM combination may also more effectively antagonize the effect of ASA on the vascular endothelium and thus spares its PG $I_2$ production. The favorable effect of SAM would be further aided by its high first-pass effect which permits its ASA-protective action to be limited to the presystemic (portal and mesenteric) circulation where ASA optimally exerts its antithrombotic effect.

While certain embodiments of the invention have been described herein in detail, numerous alternative embodiments of the invention are contemplated as falling within the claims. Consequently, the scope of the invention is not limited to the specific teachings contained herein.

What is claimed is:

1. A method of treating a coagulation disorder in a mammalian patient in need of such treatment, which comprises administering to said patient an anticoagulant-effective amount of a combination of aspirin and salicylamide which comprises a dose of 10–20 mg/kg body weight aspirin and a dose of 3–10 mg/kg body weight salicylamide.

2. A method in accordance with claim 1 wherein said aspirin and salicylamide are administered in a single dosage form.

3. A method in accordance with claim 1, wherein said aspirin and salicylamide are co-administered in separate dosage forms.

4. A method in accordance with claim 1 wherein said aspirin and salicylamide are administered orally.

5. A method of enhancing the anticoagulant effect of aspirin in a mammal in need of such treatment, comprising administering to said mammal, in connection with a dose of aspirin, an aspirin-anticoagulant enhancing effective amount of salicylamide wherein the aspirin is administered in an amount ranging from about 10 to 20 mg/kg body weight, and the salicylamide is administered in an amount ranging from about 3 to 9 mg/kg of body weight.

6. A method in accordance with claim 5 wherein the aspirin and salicylamide are administered in a combination dosage form.

7. A method in accordance with claim 5 wherein the aspirin and salicylamide are co-administered in separate dosage forms.

8. A method in accordance with claim 5 wherein the aspirin/salicylamide combination dosage administered is about 20/6 mg/kg body weight.

9. A method in accordance with claim 5 wherein the aspirin/salicylamide combination dosage administered is about 10/9 mg/kg body weight.

10. In a method of treating a coagulation disorder in a patient in need of such treatment, wherein such patient treated for such coagulation disorders with an anticoagulating dose of aspirin comprising a dose of 10–20 mg/kg body, weight, the improvement comprising adminstering to said patient an effective amount of salicylamide comprising a dose of 3–10 mg/kg body weight to enhance said treatment.

11. In the method of claim 10, the improvement comprising the co-administration of bout 3–9 mg/kg salicylamide.

12. In the method of claim 10, the improvement comprising the oral co-administration of about 3–9 mg/kg salicylamide.

* * * * *